United States Patent
Pierce et al.

(10) Patent No.: US 10,241,115 B2
(45) Date of Patent: Mar. 26, 2019

(54) IMMUNOHISTOCHEMICAL PROXIMITY ASSAY FOR PD-1 POSITIVE CELLS AND PD-LIGAND POSITIVE CELLS IN TUMOR TISSUE

(71) Applicant: Merck Sharp & Dohme Corp., Rahway, NJ (US)

(72) Inventors: Robert H. Pierce, San Francisco, CA (US); Jennifer H. Yearley, Palo Alto, CA (US); Scott P. Turner, Sunnyvale, CA (US); Belma Dogdas, Secaucus, NJ (US); Ansuman Bagchi, Plainsboro, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/103,050

(22) PCT Filed: Dec. 8, 2014

(86) PCT No.: PCT/US2014/068980
§ 371 (c)(1),
(2) Date: Jun. 9, 2016

(87) PCT Pub. No.: WO2015/088930
PCT Pub. Date: Jun. 18, 2015

(65) Prior Publication Data
US 2016/0305947 A1    Oct. 20, 2016

Related U.S. Application Data

(60) Provisional application No. 61/914,267, filed on Dec. 10, 2013.

(51) Int. Cl.
| | | |
|---|---|---|
| G06T 7/00 | (2017.01) | |
| G06T 7/11 | (2017.01) | |
| G06T 7/41 | (2017.01) | |
| G06T 7/90 | (2017.01) | |
| A61K 39/00 | (2006.01) | |
| C07K 16/28 | (2006.01) | |
| G06F 19/00 | (2018.01) | |
| G01N 33/574 | (2006.01) | |
| C12Q 1/6886 | (2018.01) | |

(52) U.S. Cl.
CPC ... *G01N 33/57492* (2013.01); *C07K 16/2818* (2013.01); *C12Q 1/6886* (2013.01); *G01N 33/574* (2013.01); *G06F 19/00* (2013.01); *G06F 19/34* (2013.01); *G06T 7/0012* (2013.01); *G06T 7/11* (2017.01); *G06T 7/41* (2017.01); *G06T 7/90* (2017.01); *A61K 2039/505* (2013.01); *C07K 2317/76* (2013.01); *C12Q 2600/158* (2013.01); *G01N 2333/70521* (2013.01); *G01N 2333/70532* (2013.01); *G01N 2800/52* (2013.01); *G06T 2207/10024* (2013.01); *G06T 2207/10056* (2013.01); *G06T 2207/10064* (2013.01); *G06T 2207/20021* (2013.01); *G06T 2207/30024* (2013.01); *G06T 2207/30096* (2013.01); *G06T 2207/30204* (2013.01)

(58) Field of Classification Search
None
See application file for complete search history.

(56) References Cited

U.S. PATENT DOCUMENTS

| | | |
|---|---|---|
| 7,521,051 B2 | 4/2009 | Collins et al. |
| 8,008,449 B2 | 8/2011 | Korman et al. |
| 8,354,509 B2 | 1/2013 | Carven et al. |
| 8,383,796 B2 | 2/2013 | Korman et al. |
| 8,583,380 B2 | 11/2013 | Stephan et al. |
| 2010/0254589 A1 | 10/2010 | Gallagher |
| 2010/0266617 A1 | 10/2010 | Carven et al. |
| 2013/0309250 A1* | 11/2013 | Cogswell ........... C07K 16/2827 424/172.1 |

FOREIGN PATENT DOCUMENTS

| | | |
|---|---|---|
| WO | WO2008156712 | 12/2008 |
| WO | WO2010027827 | 3/2010 |
| WO | WO2010077634 | 7/2010 |
| WO | WO2011066342 | 6/2011 |
| WO | WO2013019906 | 2/2013 |

OTHER PUBLICATIONS

Ahmadzadeh et al., Tumor antigen-specific CD8 T cells infiltrating the tumor express high levels of PD-1 and are functionally impaired, Blood, 2009, 1537-1544, 114.

Dong et al., Tumor-associated B7-H1 promotes T-cell apoptosis: A potential mechanism of immune evasion, Nature Medicine, 2002, 793-800, 8(8).

Gadiot et al., Overall Survival and PD-L1 Expression in Metastasized Malignant Melanoma, Cancer, 2011, 2192-2201, 117.

Gao et al., Overexpression of PD-L1 Significantly Associates with Tumor Aggressiveness and Postoperative Recurrence in Human Hepatocellular Carcinoma, Clinical Cancer Research, 2009, 971-979, 15.

(Continued)

*Primary Examiner* — Peter J Reddig
(74) *Attorney, Agent, or Firm* — Alysia A. Finnegan; Laura M. Ginkel

(57) ABSTRACT

The present disclosure describes an IHC assay for detecting and quantifying spatially proximal pairs of PD-1-expressing cells (PD-1+ cells) and PD-Ligand-expressing cells (PD-L+ cells) in tumor tissue, and the use of the assay to generate proximity biomarkers that are predictive of which cancer patients are most likely to benefit from treatment with a PD-1 antagonist. The disclosure also provides methods for testing tumor samples for the proximity biomarkers, as well as methods for treating subjects with a PD-1 antagonist based on the test results.

18 Claims, 23 Drawing Sheets
(7 of 23 Drawing Sheet(s) Filed in Color)

Specification includes a Sequence Listing.

(56) References Cited

OTHER PUBLICATIONS

Ghebeh et al., FOXP3+ Tregs and B7-H1+/PD-1+T lymphocytes co-infiltrate the tumor tissues of high-risk breast cancer patients: Implication for immunotherapy, BMC Cancer, 2008, 57-68, 8.

Ghebeh et al., The B7-H1 (PD-L1) T Lymphocyte-Inhibitory Molecule Is Expressed in Breast Cancer Patients with Infiltrating Ductal Carcinoma: Correlation with Important High-Risk Prognostic Factors, Neoplasia, 2006, 190-198, 8.

Hamanishi et al., Programmed cell death 1 ligand 1 and tumor-infiltrating CD8+ T lymphocytes are prognostic factors of human ovarian cancer, Proceedings of the National Academy of Sciences USA, 2007, 3360-3365, 104.

Hamid et al., Safety and Tumor Responses with Lambrolizumab (Anti-PD-1) in Melanoma, New Eng. J. Med., 2013, 134-144, 369(2).

Hino et al., Tumor cell expression of programmed cell death-1 ligand 1 is a prognostic factor for malignant melanoma, Cancer, 2010, 1757-1766, 116(7).

Inman et al., PD-L1 (B7-H1) expression by urothelial carcinoma of the bladder and BCG-induced granulomata: associations with localized stage progression, Cancer, 2007, 1499-1505, 109.

Nakanishi et al., Overexpression of B7-H1 (PD-L1) significantly associates with tumor grade and postoperative prognosis in human urothelial cancers, Cancer Immunol. Immunother., 2007, 1173-1182, 56.

Nomi et al., Clinical Significance and Therapeutic Potential of the Programmed Death-1 Ligand/Programmed Death-1 Pathway in Human Pancreatic Cancer, Clinical Cancer Research, 2007, 2151-2157, 13.

Ohigashi et al., Clinical Significance of Programmed Death-1 Ligand-1 and Programmed Death-1 Ligand-2 Expression in Human Esophageal Cancer, Clin. Cancer Research, 2005, 2947-2953, 11.

Sharpe et al., The function of programmed cell death 1 and its ligands in regulating autoimmunity and infection, Nature Immunology, 2007, 239-245, 8.

Shimauchi et al., Augmented expression of programmed death-1 in both neoplastic and non-neoplastic CD4+ T-Cells in adult T-cell leukemia/lymphoma, Int. J. Cancer, 2007, 2585-2590, 121.

Spigel et al., Clinical activity, safety, and biomarkers of MPDL3280A, an engineered PD-L1 antibody in patients with locally advanced or metastatic non-small cell lung cancer (NSCLC)., J. Clin. Oncol., 2013, Abstract 8008, Suppl 31.

Taube et al., Colocalization of Inflammatory Response with B7-H1 Expression in Human Melanocytic Lesions Supports an Adaptive Resistance Mechanism of Immune Escape, Sci. Transl. Med., 2012, 127ra37, 1-10, 4(127).

Thompson et al., Costimulatory B7-H1 in renal cell carcinoma patients: Indicator of tumor aggressiveness and potential therapeutic target, Proc. Nat'l Acad. Sci. USA, 2004, 17174-17179, 101(49).

Thompson et al., PD-1 Is Expressed by Tumor-Infiltrating Immune Cells and Is Associated with Poor Outcome for Patients with Renal Cell Carcinoma, Clinical Cancer Research, 2007, 1757-1761, 15.

Thompson et al., Tumor B7-H1 Is Associated with Poor Prognosis in Renal Cell Carcinoma Patients with Long-Term Follow-up, Cancer Res., 2006, 3381-3385, 66.

Topalian et al., Safety, Activity, and Immune Correlates of Anti-PD-1 Antibody in Cancer, New Eng. J. Med., 2012, 2443-2454, 366(26).

Wang, et al., Immunostaining of PD-1/PD-Ls in liver tissues of patients with hepatitis and hepatocellular carcinoma, World J. Gastroenterol., 2011, 3322-3329, 17.

Yang et al., PD-L1: PD-1 Interaction Contributes to the Functional Suppression of T-Cell Responses to Human Uveal Melanoma Cells In Vitro, Invest Ophthalmol Vis Sci, 2008, 2518-2525, 49(6).

Angell et al., Digital pattern recognition-based image analysis quantifies immune infiltrates in distinct tissue regions of colorectal cancer, British Journal of Cancer, 2013, pp. 1618-1624, vol. 109, No. 6.

Bigelow et al., Immunohistochemical Staining of B7-H1 (PD-L1) on Paraffin-embedded Slides of Pancreatic Adenocarcinoma Tissue, Journal of Visualized Experiments, 2013, e4059 (1-6), No. 71.

Brusa et al., The PD-1/PD-L1 axis contributes to T-cell dysfunction in chronic lymphocytic leukemia, Haematologica, 2013, pp. 953-963, vol. 98, No. 6.

Kluger et al., Drug targets and predictive biomarkers in the management of metastatic melanoma, Pharmacogenomics and Personalized Medicine, 2012, pp. 139-148, vol. 5.

Tumeh et al., PD-1 blockade induces responses by inhibiting adaptive immune resistance, Nature, 2014, pp. 568-571, vol. 515, No. 7528.

\* cited by examiner

| Disc Number | Green Pixels | Red Pixels | | Proximity Call |
|---|---|---|---|---|
| 1 | 0 | 13 | | Negative |
| 2 | 13 | 0 | | Negative |
| 3 | 13 | 13 | | Positive |
| 4 | 0 | 0 | | Negative |
| 5 | 7 | 3 | | Positive |

FIG.3B

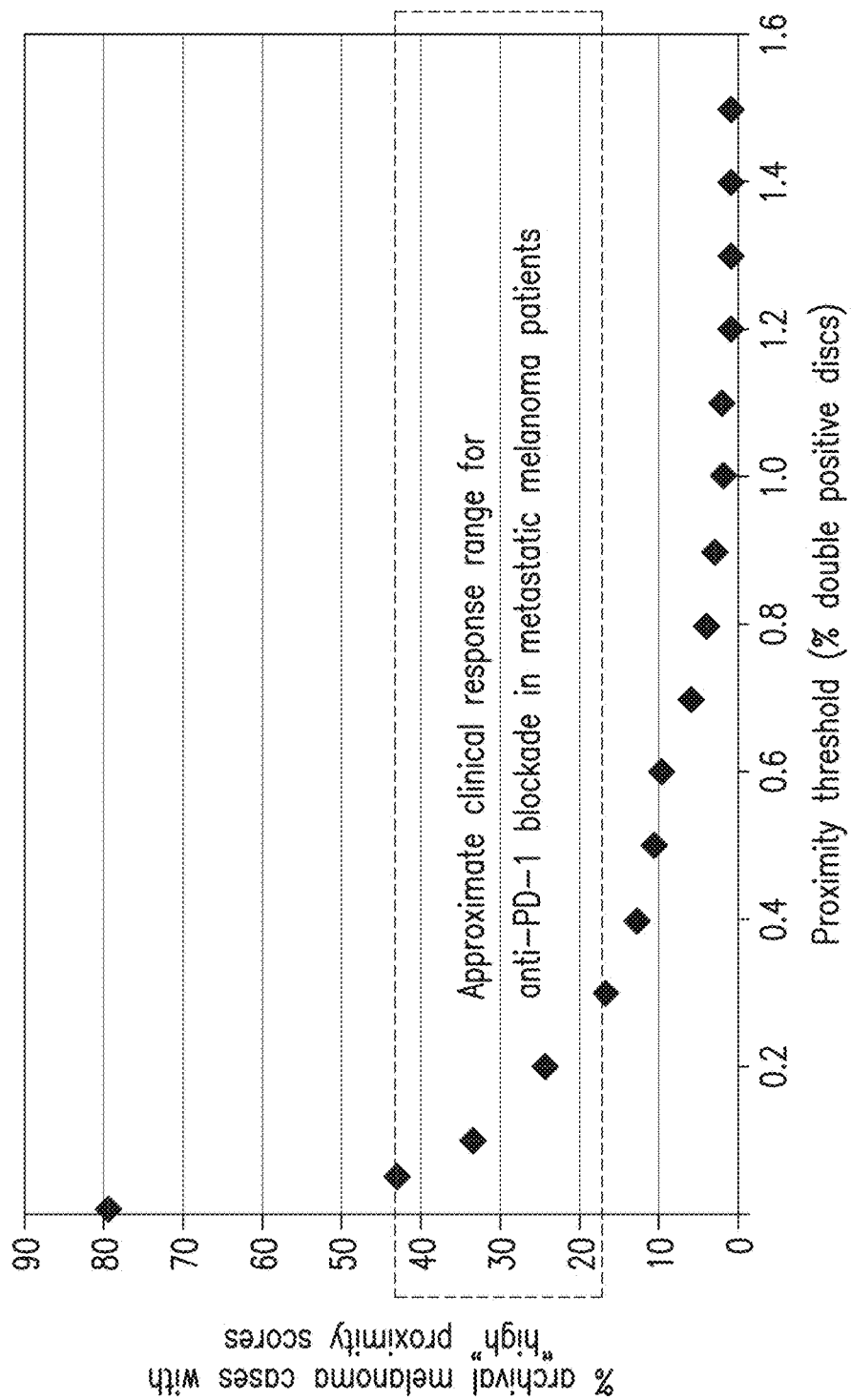

hPD-1.08A light chain CDR1 (SEQ ID NO:1)

Arg Ala Ser Lys Ser Val Ser Thr Ser Gly Phe Ser Tyr Leu His hPD-1.08A light chain CDR2 (SEQ ID NO:2)

Leu Ala Ser Asn Leu Glu Ser hPD-1-08A light chain CDR3 (SEQ ID NO:3)

Gln His Ser Trp Glu Leu Pro Leu Thr hPD-1.08A heavy chain CDR1 (SEQ ID NO:4)

Ser Tyr Tyr Leu Tyr hPD-1.08A heavy chain CDR2 (SEQ ID NO:5)

Gly Val Asn Pro Ser Asn Gly Gly Thr Asn Phe Ser Glu Lys Phe Lys Ser hPD-1.08A heavy chain CDR3 (SEQ ID NO:6)

Arg Asp Ser Asn Tyr Asp Gly Gly Phe Asp Tyr

FIG.9 hPD-1.09A light chain CDR1 (SEQ ID NO:7)

Arg Ala Ser Lys Gly Val Ser Thr Ser Gly Tyr Ser Tyr Leu His hPD-1.09A light chain CDR2 (SEQ ID NO:8)

Leu Ala Ser Tyr Leu Glu Ser hPD-1.09A light chain CDR3 (SEQ ID NO:9)

Gln His Ser Arg Asp Leu Pro Leu Thr hPD-1.09A heavy chain CDR1 (SEQ ID NO:10)

Asn Tyr Tyr Met Tyr hPD-1.09A heavy chain CDR2 (SEQ ID NO:11)

Gly Ile Asn Pro Ser Asn Gly Gly Thr Asn Phe Asn Glu Lys Phe Lys Asn hPD-1.09A heavy chain CDR3 (SEQ ID NO:12)

Arg Asp Tyr Arg Phe Asp Met Gly Phe Asp Tyr

FIG.10

109A-H heavy chain variable region (SEQ ID NO:13)

Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser

409A-H heavy chain full length (SEQ ID NO:14)

Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser Ala Ser Thr Lys Gly Pro Ser Val Phe Pro Leu Ala Pro
Cys Ser Arg Ser Thr Ser Glu Ser Thr Ala Ala Leu Gly Cys Leu Val Lys Asp Tyr
Phe Pro Glu Pro Val Thr Val Ser Trp Asn Ser Gly Ala Leu Thr Ser Gly Val His
Thr Phe Pro Ala Val Leu Gln Ser Ser Gly Leu Tyr Ser Leu Ser Ser Val Val Thr
Val Pro Ser Ser Ser Leu Gly Thr Lys Thr Tyr Thr Cys Asn Val Asp His Lys Pro
Ser Asn Thr Lys Val Asp Lys Arg Val Glu Ser Lys Tyr Gly Pro Pro Cys Pro Pro
Cys Pro Ala Pro Glu Phe Leu Gly Gly Pro Ser Val Phe Leu Phe Pro Pro Lys Pro
Lys Asp Thr Leu Met Ile Ser Arg Thr Pro Glu Val Thr Cys Val Val Val Asp Val
Ser Gln Glu Asp Pro Glu Val Gln Phe Asn Trp Tyr Val Asp Gly Val Glu Val His
Asn Ala Lys Thr Lys Pro Arg Glu Glu Gln Phe Asn Ser Thr Tyr Arg Val Val Ser
Val Leu Thr Val Leu His Gln Asp Trp Leu Asn Gly Lys Glu Tyr Lys Cys Lys Val
Ser Asn Lys Gly Leu Pro Ser Ser Ile Glu Lys Thr Ile Ser Lys Ala Lys Gly Gln
Pro Arg Glu Pro Gln Val Tyr Thr Leu Pro Pro Ser Gln Glu Glu Met Thr Lys Asn
Gln Val Ser Leu Thr Cys Leu Val Lys Gly Phe Tyr Pro Ser Asp Ile Ala Val Glu
Trp Glu Ser Asn Gly Gln Pro Glu Asn Asn Tyr Lys Thr Thr Pro Pro Val Leu Asp
Ser Asp Gly Ser Phe Phe Leu Tyr Ser Arg Leu Thr Val Asp Lys Ser Arg Trp Gln
Glu Gly Asn Val Phe Ser Cys Ser Val Met His Glu Ala Leu His Asn His Tyr Thr
Gln Lys Ser Leu Ser Leu Ser Leu Gly Lys

FIG.11

K09A-L-11 light chain variable region (SEQ ID NO:15)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys

K09A-L-16 light chain variable region (SEQ ID NO:16)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys

K09A-L-17 light chain variable region (SEQ ID NO:17)

Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys

FIG.12

K09A-L-11 light chain full length (SEQ ID NO:18)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

FIG.13A

K09A-L-16 light chain full length (SEQ ID NO:19)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

FIG.13B

K09A-L-17 light chain full length (SEQ ID NO:20)

Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

Heavy chain (SEQ ID NO:21)

| | | | | | |
|---|---|---|---|---|---|
| QVQLVQSGVE | VKKPGASVKV | SCKASGYTFT | NYYMYWVRQA | PGQGLEWMGG | 50 |
| INPSNGGTNF | NEKFKNRVTL | TTDSSTTTAY | MELKSLQFDD | TAVYYCARRD | 100 |
| YRFDMGFDYW | GQGTTVTVSS | ASTKGPSVFP | LAPCSRSTSE | STAALGCLVK | 150 |
| DYFPEPVTVS | WNSGALTSGV | HTFPAVLQSS | GLYSLSSVVT | VPSSSLGTKT | 200 |
| YTCNVDHKPS | NTKVDKRVES | KYGPPCPPCP | APEFLGGPSV | FLFPPKPKDT | 250 |
| LMISRTPEVT | CVVVDVSQED | PEVQFNWYVD | GVEVHNAKTK | PREEQFNSTY | 300 |
| RVVSVLTVLH | QDWLNGKEYK | CKVSNKGLPS | SIEKTISKAK | GQPREPQVYT | 350 |
| LPPSQEEMTK | NQVSLTCLVK | GFYPSDIAVE | WESNGQPENN | YKTTPPVLDS | 400 |
| DGSFFLYSRL | TVDKSRWQEG | NVFSCSVMHE | ALHNHYTQKS | LSLSLGK | 447 |

Light chain (SEQ ID NO:22)

| | | | | | |
|---|---|---|---|---|---|
| EIVLTQSPAT | LSLSPGERAT | LSCRASKGVS | TSGYSYLHWY | QQKPGQAPRL | 50 |
| LIYLASYLES | GVPARFSGSG | SGTDFTLTIS | SLEPEDFAVY | YCQHSRDLPL | 100 |
| TFGGGTKVEI | KRTVAAPSVF | IFPPSDEQLK | SGTASVVCLL | NNFYPREAKV | 150 |
| QWKVDNALQS | GNSQESVTEQ | DSKDSTYSLS | STLTLSKADY | EKHKVYACEV | 200 |
| THQGLSSPVT | KSFNRGEC | | | | 219 |

FIG.14

Nivolumab

Heavy chain (SEQ ID NO:23)

| | | | | | |
|---|---|---|---|---|---|
| QVQLVESGGG | VVQPGRSLRL | DCKASGITFS | NSGMHWVRQA | PGKGLEWVAV | 50 |
| IWYDGSKRYY | ADSVKGRFTI | SRDNSKNTLF | LQMNSLRAED | TAVYYCATND | 100 |
| DYWGQGTLVT | VSSASTKGPS | VFPLAPCSRS | TSESTAALGC | LVKDYFPEPV | 150 |
| TVSWNSGALT | SGVHTFPAVL | QSSGLYSLSS | VVTVPSSSLG | TKTYTCNVDH | 200 |
| KPSNTKVDKR | VESKYGPPCP | PCPAPEFLGG | PSVFLFPPKP | KDTLMISRTP | 250 |
| EVTCVVVDVS | QEDPEVQFNW | YVDGVEVHNA | KTKPREEQFN | STYRVVSVLT | 300 |
| VLHQDWLNGK | EYKCKVSNKG | LPSSIEKTIS | KAKGQPREPQ | VYTLPPSQEE | 350 |
| MTKNQVSLTC | LVKGFYPSDI | AVEWESNGQP | ENNYKTTPPV | LDSDGSFFLY | 400 |
| SRLTVDKSRW | QEGNVFSCSV | MHEALHNHYT | QKSLSLSLGK | | 440 |

Light chain (SEQ ID NO:24)

| | | | | | |
|---|---|---|---|---|---|
| EIVLTQSPAT | LSLSPGERAT | LSCRASQSVS | SYLAWYQQKP | GQAPRLLIYD | 50 |
| ASNRATGIPA | RFSGSGSGTD | FTLTISSLEP | EDFAVYYCQQ | SSNWPRTFGQ | 100 |
| GTKVEIKRTV | AAPSVFIFPP | SDEQLKSGTA | SVVCLLNNFY | PREAKVQWKV | 150 |
| DNALQSGNSQ | ESVTEQDSKD | STYSLSSTLT | LSKADYEKHK | VYACEVTHQG | 200 |
| LSSPVTKSFN | RGEC | | | | 214 |

FIG.15

Antibody 22C3

Heavy Chain

QVHLQQSGAELAKPGASVKMSCKASGYTFTSYWIHWIKQRPGQGLEWIGYINPSSGYHEYNQKFIDKATL
TADRSSSTAYMHLTSLTSEDSAVYYCARSGWLIHGDYYFDFWGQGTTLTVSSAKTTPPSVYPLAPGSAAQ
TNSMVTLGCLVKGYFPEPVTVTWNSGSLSSGVHTFPAVLQSDLYTLSSSVTVPSSTWPSETVTCNVAHPA
SSTKVDKKIVPRDCGCKPCICTVPEVSSVFIFPPKPKDVLTITLTPKVTCVVVDISKDDPEVQFSWFVDD
VEVHTAQTQPREEQFNSTFRSVSELPIMHQDWLNGKEFKCRVNSAAFPAPIEKTISKTKGRPKAPQVYTI
PPPKEQMAKDKVSLTCMITDFFPEDITVEWQWNGQPAENYKNTQPIMDTDGSYFVYSKLNVQKSNWEAGN
TFTCSVLHEGLHNHHTEKSLSHSPGK (SEQ ID NO:25)

Light Chain

DIVMSQSPSSLAVSAGEKVTMTCKSSQSLLHTSTRKNYLAWYQQKPGQSPKLLIYWASTRESGVPDRFTG
SGSGTDFTLTISSVQAEDLAVYYCKQSYDVVTFGAGTKLELKRADAAPTVSIFPPSSEQLTSGGASVVCF
LNNFYPKDINVKWKIDGSERQNGVLNSWTDQDSKDSTYSMSSTLTLTKDEYERHNSYTCEATHKTSTSPI
VKSFNRNEC (SEQ ID NO:26)

FIG.16

Chimeric anti-human PD-L1 antibody (22C3Fab:ratFc)

Heavy Chain

QVHLQQSGAELAKPGASVKMSCKASGYTFTSYWIHWIKQRPGQGLEWI**GYINPSSGYHEYN
QKFIDKATLTADRSSSTAYMHLTSLTSEDSAVYYCARSGWLIHGDYYFDF**WGQGTTLTVSS
AETTAPSVYPLAPGTALKSNSMVTLGCLVKGYFPEPVTVTWNSGALSSGVHTFPAVLQSGL
YTLTSSVTVPSSTWPSQTVTCNVAHPASSTKVDKKIVPRNCGGDCKPCICTGSEVSSVFIF
PPKPKDVLTITLTPKVTCVVVDISQDDPEVHFSWFVDDVEVHTAQTRPPEEQFNSTFRSVS
ELPILHQDWLNGRTFRCKVTSAAFPSPIEKTISKPEGRTQVPHVYTMSPTKEEMTQNEVSI
TCMVKGFYPPDIYVEWQMNGQPQENYKNTPPTMDTDGSYFLYSKLNVKKEKWQQGNTFTCS
VLHEGLHNHHTEKSLSHSPGK (SEQ ID NO:27)

Light Chain

MSQSPSSLAVSAGEKVTMTCKSSQSLLHTSTRKNYLAWYQQKPGQSPKLLIYWASTRESGV
PDRFTGSGSGTDFTLTISSVQAEDLAVYYCKQSYDVVTFGAGTKLELKRADAAPTVSIFPP
STEQLATGGASVVCLMNNFYPRDISVKWKIDGTERRDGVLDSVTDQDSKDSTYSMSSTLSL
TKADYESHNLYTCEVVHKTSSSPVVKSFNRNEC (SEQ ID NO:28)

FIG.17

Mouse anti-human PD-L1 Antibody 20C3

Heavy Chain Variable Region

Q V Q V Q Q S G A E L A E P G A S V K M S C K A S G Y I F T <u>S Y W M H</u>
W L K Q R P G Q G L E W I G <u>Y I N P S S D Y N E Y S E K F M D</u> K A T L
T A D K A S T T A Y M Q L I S L T S E D S A V Y Y C A R <u>S G W L V H G</u>
<u>D Y Y F D Y</u> W G Q G T T L T V S S (SEQ ID NO:29)

Light Chain Variable Region

D I V M S Q S P S S L A V S A G E K V T M S C <u>K S S Q S L L N S R T R</u>
<u>K N Y L A</u> W Y Q Q K P G Q S P K L L I Y <u>W A S T R E S</u> G V P D R F T G
S G S G T D F T L T I S S V Q A E D L A V Y Y C <u>Q Q S Y D V V T</u> F G A
G T K L E L K (SEQ ID NO:30)

FIG.18

IMMUNOHISTOCHEMICAL PROXIMITY ASSAY FOR PD-1 POSITIVE CELLS AND PD-LIGAND POSITIVE CELLS IN TUMOR TISSUE

FIELD OF THE INVENTION

The present invention relates generally to the treatment of cancer. In particular, the invention relates to the identification of biomarkers for identifying patients whose tumors are likely to respond to treatment with an antagonist of Programmed Death 1 (PD-1).

CROSS-REFERENCE TO RELATED APPLICATIONS

This application is a § 371 National Phase Application of International Application No. PCT/US2014/068980, filed Dec. 8, 2014, which claims the benefit of U.S. Application No. 61/914,267, filed Dec. 10, 2013.

REFERENCE TO SEQUENCE LISTING SUBMITTED ELECTRONICALLY

The sequence listing of the present application is submitted electronically via EFS-Web as an ASCII formatted sequence listing with a file name "23668USPCT-SEQLIST-07JUN2016.TXT", creation date of May 25, 2016, and a size of 41.5 KB. This sequence listing submitted EFS-Web is part of the specification and is herein incorporated by reference in its entirety.

BACKGROUND OF THE INVENTION

PD-1 is recognized as an important player in immune regulation and the maintenance of peripheral tolerance. PD-1 is moderately expressed on naive T, B and NKT cells and up-regulated by TB cell receptor signaling on lymphocytes, monocytes and myeloid cells (1). Two known ligands for PD-1, PD-L1 (B7-H1) and PD-L2 (B7-DC), are expressed in human cancers arising in various tissues, and PD-L1 expression has been associated with poor prognosis and reduced overall survival, irrespective of subsequent treatment, in studies on different cancers, e.g., ovarian, renal, colorectal, pancreatic, liver cancers and melanoma (2-12). Similarly, PD-1 expression on tumor infiltrating lymphocytes was found to mark dysfunctional T cells in breast cancer and melanoma (13-15) and to correlate with poor prognosis in renal cancer (16). Thus, it has been proposed that PD-L1 expressing tumor cells interact with PD-1 expressing T cells to attenuate T cell activation and evasion of immune surveillance, thereby contributing to an impaired immune response against the tumor.

Several monoclonal antibodies that inhibit the interaction between PD-1 and one or both of its ligands PD-L1 and PD-L2 are in clinical development for treating cancer. These include nivolumab and MK-3475, which are antibodies that bind to PD-1, and MPDL3280A, which binds to PD-L1 (17-19). While clinical studies with these antibodies have produced durable anti-tumor responses in some cancer types, a significant number of patients failed to exhibit an anti-tumor response.

Tumor expression of PD-L1 has been investigated as a predictive biomarker to identify tumors that are likely to respond to anti-PD-1 blockade, and published studies have generally described immunohistochemistry (IHC) analysis of frozen or formalin-fixed, paraffin-embedded (FFPE) tumor tissue sections stained with a primary antibody that binds to PD-L1 (20-23). These and other studies have shown that while tumor PD-L1 expression appears to be positively correlated with a greater chance of response to treatment with a PD-1 antagonist, anti-tumor responses to PD-1 antagonists have been observed in a significant number of patients who were designated as PD-L1 negative by IHC assay. Thus, a need exists for diagnostic tools to identify which cancer patients are most likely to achieve a clinical benefit to treatment with a PD-1 antagonist.

SUMMARY OF THE INVENTION

The inventors have discovered that quantifying the number of PD-1-expressing cells (PD-1+ cells) that are spatially proximal with PD-L1-expressing cells (PD-L1+ cells) in tumor samples is a useful tool to predict which patients are most likely to respond to treatment with a PD-1 antagonist. To facilitate the detection and quantitation of such spatially proximal cells in a tumor sample, the inventors developed a mutliparametric IHC proximity assay, which employs a PD-1-binding antibody, a PD-L1-binding antibody and a random sampling algorithm to generate a proximity score for a tumor tissue section that represents the number of tumor associated pairs of spatially proximal PD-1+ cells and PD-L1+ cells, i.e., cells that are situated within a physiologically relevant distance of each other.

As described in more detail below, the inventors also demonstrated the utility of the proximity scores generated by this assay to identify patients who are most likely to respond to treatment with a PD-1 antagonist using a cohort of 15 melanoma patients treated with MK-3475. By comparing pre-treatment tumor proximity scores with clinical response data, the inventors identified a threshold, or cut-off, proximity score that partitions responders from nonresponders and negative with greater than 85% accuracy: a positive predictive value of 0.889 for a high proximity score (at or above the selected threshold) and a negative predictive value of 1.000 for a low proximity score (below the selected threshold).

The inventors contemplate that this IHC proximity assay and the proximity scores generated thereby will be useful to identify proximity threshold scores that can serve as biomarkers to predict response of multiple tumor types to treatment with a PD-1 antagonist.

Thus, in one aspect, the present invention provides a process for assigning a PD-1:PD-Ligand proximity score to a tumor sample. The process comprises obtaining an image of tissue that has been removed from the tumor sample and immunohistochemically stained for PD-1 and PD-Ligand expression in a manner that allows stained PD-1 cells to be distinguished from stained PD-Ligand cells, defining in the image at least one region of interest (ROI) that comprises neoplastic cells and associated stroma, randomly creating across each defined ROI a plurality of subregions of substantially the same shape and size, and calculating the percent of all of the subregions that are positive for both stained PD-1 cells and stained PD-Ligand cells to generate the PD-1:PD-ligand proximity score for the tumor sample.

All of the defined ROIs combined together comprise substantially all of the neoplastic cells and associated stroma in the image. In some embodiments, the image represents the entirety of the stained tissue and a single ROI is defined to comprise substantially all of the neoplastic cells and associated stroma that are visible in the image. In other embodiments, the image represents the entirety of the stained tissue and multiple ROIs are defined to comprise substantially all of the neoplastic cells and associated stroma. In all embodiments, each of the randomly created subregions defines an area that is large enough to include a spatially proximal pair of a stained PD-1 cell and a stained PD-Ligand cell, and preferably small enough to exclude pairs of stained PD-1 and PD-Ligand cells that are not spatially proximal.

In some preferred embodiments, defining an ROI comprises inspecting the image to identify neoplastic cells and associated stroma, and then applying to the image a boundary that surrounds the identified neoplastic cells and associated stroma. In other preferred embodiments, the tumor sample has been immunohistochemically stained for expression of a tumor-specific marker protein, and defining an ROI comprises assigning a boundary that mirrors the boundary of the tumor-specific staining.

In some embodiments, the tissue has been immunohistochemically stained for expression of either or both of PD-L1 and PD-L2, and in preferred embodiments, the tissue has been stained only for PD-L1 expression.

In some embodiments, the tissue has been counterstained to provide contrast to the PD-1 and PD-Ligand staining, and preferably the tissue has been counterstained with a nuclear stain.

In some embodiments, the stained tissue is comprised of a single tissue section that has been stained in a multiplex immunohistochemistry (IHC) assay. In such embodiments, the image is obtained by a method comprising contacting the tissue section with an antibody specific for PD-1 (anti-PD-1 Ab) and an antibody specific for the desired PD-Ligand (anti-PD-Ligand Ab) under conditions suitable for forming antibody-antigen complexes, washing the tissue section to remove unbound antibody and detecting antibody-antigen complexes comprising the PD-1 antibody or the PD-Ligand antibody. In some preferred embodiments, the tissue section is stained with the anti-PD-1 and anti-PD-Ligand Abs simultaneously, and in other preferred embodiments, the IHC assay comprises staining with one of the antibodies followed by staining with the other antibody and may be done in either order.

In other embodiments, the stained tissue is comprised of at least two adjacent tissue sections that have been stained in separate monoplex IHC assays, wherein one of the tissue sections has been stained for PD-1 using the anti-PD-1 Ab and the other tissue section has been stained for the PD-Ligand using the anti-PD-Ligand Ab. In such embodiments, the image is obtained by creating a registered digital image of each of the stained tissue sections, and superimposing the two digital images to generate a composite image.

In other embodiments, cells that express PD-1 may be detected by immunohistochemically staining for expression of a molecule that extensively co-localizes with PD-1 and similarly, cells that express the PD-Ligand of interest may be detected by immunohistochemically staining for expression of a molecule that extensively co-localizes with the PD-Ligand. In such embodiments, an antibody that specifically binds to the co-localizing molecule is used as the primary antibody instead of the anti-PD-1 or anti-PD-Ligand antibody.

Any of the above multiplex or monoplex IHC assays may be a direct IHC assay or an indirect IHC assay. In the direct IHC assay, the anti-PD-1 Ab has a first detectable label and the anti-PD-Ligand Ab has a second detectable label that is distinguishable from the first label. For embodiments employing an indirect IHC assay, unlabeled anti-PD-1 and anti-PD Ligand Abs are used as primary antibodies, and detecting antibody-antigen complexes formed using these Abs comprises contacting the tissue section with two secondary antibodies: a secondary antibody specific for the anti-PD-1 Ab that has a first detectable label and a secondary antibody specific for anti-PD-Ligand Ab that has a second detectable label that is distinguishable from the first label. In either of the direct or indirect IHC assays, the distinguishable labels are preferably different colors produced by chromogens or fluorophores.

In some preferred embodiments, the distinguishable labels are first and second colors, the image is a digital image and the process further comprises subjecting the digital image to an automated image analysis system that segments the ROI to extract a first set of pixels for the first color and a second set of pixels for the second color, and uses the extracted pixel sets to assign positive or negative values to each of the randomly created subregions in the ROI. A positive value is assigned if the subregion has a pixel from each of the first and second extracted pixel sets and a negative value is assigned if the subregion lacks a pixel from either the first or second extracted pixel sets. In particularly preferred embodiments, the image segmentation and pixel extraction occurs prior to the creation of the subregions.

The inventors herein have also identified several types of fluorescing artifacts that are present in some images of tissues stained with two different fluorophores as the distinguishable labels. These artifact types include a low intensity autofluorescense signal across the tissue, a high intensity autofluorescence around the edges of the tissue, and a blood artifact that fluoresces brightly in the channels of both distinguishable labels. Thus, in some preferred embodiments, prior to segmenting the ROI, the automated image analysis system examines the image for each of these artifacts and removes any detected artifacts from the image.

The anti-PD-Ligand Ab used in any of the multiplex or monoplex IHC assays is specific for either or both of PD-L1 and PD-L2. In some preferred embodiments, the anti-PD-Ligand Ab is specific for PD-L1.

In another aspect of the invention, a PD-1:PD-Ligand proximity score for a tumor sample is used in a method of testing the tumor sample for the presence or absence of a PD-1:PD-Ligand proximity biomarker that is predictive of an anti-tumor response to treatment with a PD-1 antagonist. The method comprises comparing the PD-1:PD-Ligand proximity score for the tumor sample with a threshold PD-1:PD-Ligand proximity score and classifying the tumor as biomarker positive or biomarker negative. If the calculated proximity score is equal to or greater than the threshold proximity score, then the tumor is classified as positive for the PD-1:PD-Ligand proximity biomarker, and if the calculated score is less than the threshold score, then the tumor is classified as negative for the PD-1:PD-Ligand proximity biomarker. In some preferred embodiments, both of the test and threshold proximity scores are obtained using the above process for assigning a PD-1:PD-Ligand proximity score to a tumor sample.

In yet another aspect, the invention provides a method for treating a subject having a tumor which comprises determining if the tumor is positive or negative for a PD-1:PD-Ligand proximity biomarker and administering to the subject a PD-1 antagonist if the tumor is positive for the biomarker and administering to the subject a cancer treatment that does not include a PD-1 antagonist if the tumor is negative for the biomarker. In some preferred embodiments, both of the test and threshold proximity scores are obtained using the above process for assigning a PD-1:PD-Ligand proximity score to a tumor sample.

In a still further aspect, the invention provides a pharmaceutical composition comprising a PD-1 antagonist for use in a subject who has a tumor that tests positive for a PD-1:PD-Ligand proximity biomarker.

Yet another aspect of the invention is a drug product which comprises a pharmaceutical composition and prescribing information. The pharmaceutical composition comprises a PD-1 antagonist and at least one pharmaceutically acceptable excipient. The prescribing information states that the pharmaceutical composition is indicated for use in a subject who has a tumor that tests positive for a PD-1:PD-Ligand proximity biomarker.

In all of the above aspects and embodiments of the invention, the PD-1 antagonist inhibits the binding of PD-L1 to PD-1, and preferably also inhibits the binding of PD-L2 to PD-1. In some preferred embodiments, the PD-1 antagonist is a monoclonal antibody, or an antigen binding fragment thereof, which specifically binds to PD-1 or to PD-L1 and blocks the binding of PD-L1 to PD-1. In particularly preferred embodiments, the PD-1 antagonist is MK-3475 or nivolumab.

In some embodiments of any of the above aspects of the invention, the subject is a human and the cancer is a solid tumor and in some preferred embodiments, the solid tumor is bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC) or triple negative breast cancer. In some particularly preferred embodiments, the human subject has ipilimumab-naïve advanced melanoma, while in other particularly preferred embodiments the human subject has ipilimumab-refractory advanced melanoma.

In other embodiments of any of the above aspects of the invention, the subject is a human and the cancer is a Heme malignancy and in some preferred embodiments, the Heme malignancy is acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

In other particularly preferred embodiments of any of the above aspects of the invention, the tumor is metastatic melanoma, the PD-1 antagonist is MK-3475, the PD-Ligand is PD-L1 and the threshold PD-1:PD-Ligand proximity score is about 0.2%.

In other particularly preferred embodiments of any of the above aspects of the invention, an anti-tumor response is a partial response (PR) as measured by RECIST 1.1 criteria.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 illustrates the results of randomly sampling a region of interest in an FFPE tissue section from a melanoma tumor sample in accordance with one embodiment of the invention, in which

FIG. 7 is a graph showing on the Y-axis the percent of the 102 melanoma tissue samples from FIG. 5 in which the proximity score exceeds each value in a set of progressively increasing binary cut-points (i.e., threshold proximity scores) (X-axis), with the dashed box illustrating the range of clinical response rates that have been observed in clinical trials of PD-1 antagonists.

FIG. 9 shows amino acid sequences of the light chain and heavy chain CDRs for an exemplary anti-human PD-1 monoclonal antibody useful as a PD-1 antagonist in the treatment methods of the present invention (SEQ ID NOs: 1-6).

FIG. 10 shows amino acid sequences of the light chain and heavy chain CDRs for another exemplary anti-human PD-1 monoclonal antibody useful as a PD-1 antagonist in the present invention (SEQ ID NOs:7-12).

FIG. 11 shows amino acid sequences of the heavy chain variable region and full length heavy chain for an exemplary anti-human PD-1 monoclonal antibody useful in the present invention (SEQ ID NO:13 and SEQ ID NO:14).

FIG. 12 shows amino acid sequences of alternative light chain variable regions for an exemplary anti-human PD-1 monoclonal antibody useful as a PD-1 antagonist in the present invention (SEQ ID NOs:15-17).

FIGS. 13A-C show amino acid sequences of three alternative light chains for an exemplary anti-human PD-1 monoclonal antibody useful as a PD-1 antagonist in the present invention (SEQ ID NOs:18-20).

FIG. 14 shows amino acid sequences of the heavy and light chains for MK-3475 (SEQ ID NOs. 21 and 22, respectively).

FIG. 15 shows amino acid sequences of the heavy and light chains for nivolumab (SEQ ID NOs. 23 and 24, respectively).

FIG. 16 shows the amino acid sequences of the heavy and light chains for antibody 22C3 (SEQ ID NOs 25-26), which is an exemplary mouse anti-human PD-L1 IgG1 antibody useful for detecting PD-L1 expression in tumor samples according to the present invention, with underlining indicating the CDR sequences.

FIG. 17 shows the amino acid sequences of the heavy and light chains for a chimeric anti-human PD-L1 antibody (SEQ ID NOs 27-28), which comprises the Fab of the 22C3 antibody and a rat Fc, with underlining indicating the CDR sequences.

FIG. 18 shows the amino acid sequences of the mature heavy and light chain variable regions for antibody 20C3 (SEQ ID NOs 29-30), which is an exemplary mouse anti-human PD-L1 IgG1 antibody useful for detecting PD-L1 expression in tumor samples according to the present invention, with underlining indicating the CDR sequences.

DETAILED DESCRIPTION

Abbreviations

Figure 1A:
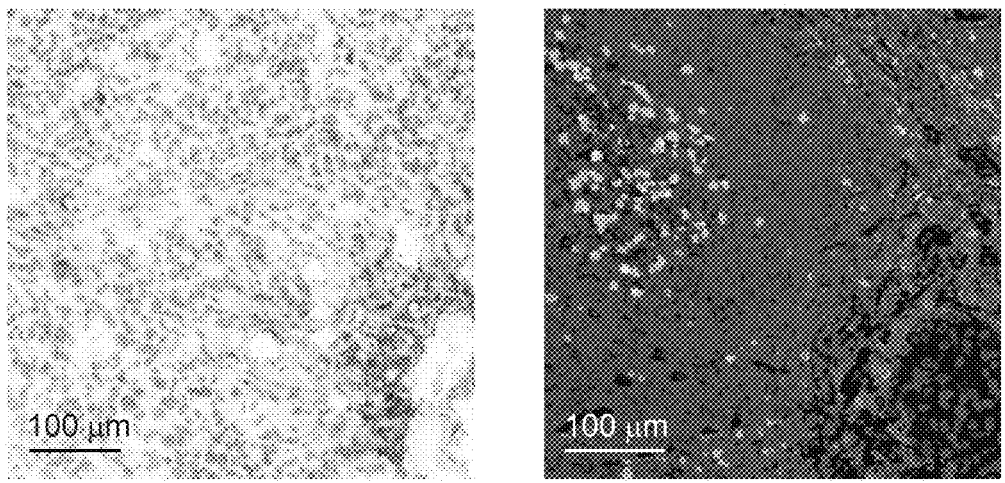
FIG. 1 shows images at 200× magnification of adjacent tissue sections of four melanoma tumor samples (FIGS. 1A, 1B, 1C and 1D) that have been immunohistochemically stained for PD-L1 expression in a monoparametric chromogenic IHC assay using an anti-PD-L1 antibody (mAb) and the brown DAB chromogen (left column) or immunohistochemically stained for PD-L1 expression and PD-1 expression in a multiparametric fluorescence IHC assay using an anti-PD1 antibody (green) and the mouse anti-PD-L1 mAb (red) (right column).
Figure 1B:
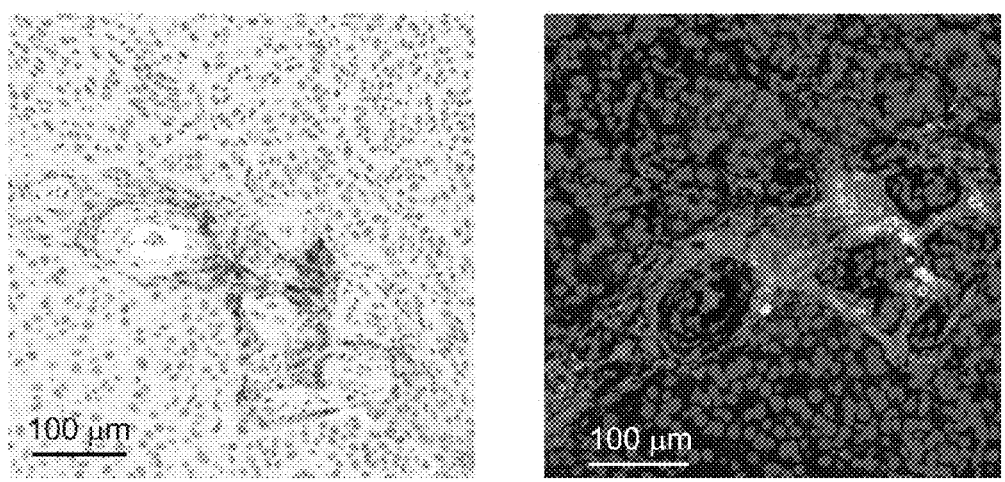
Figure 1C:
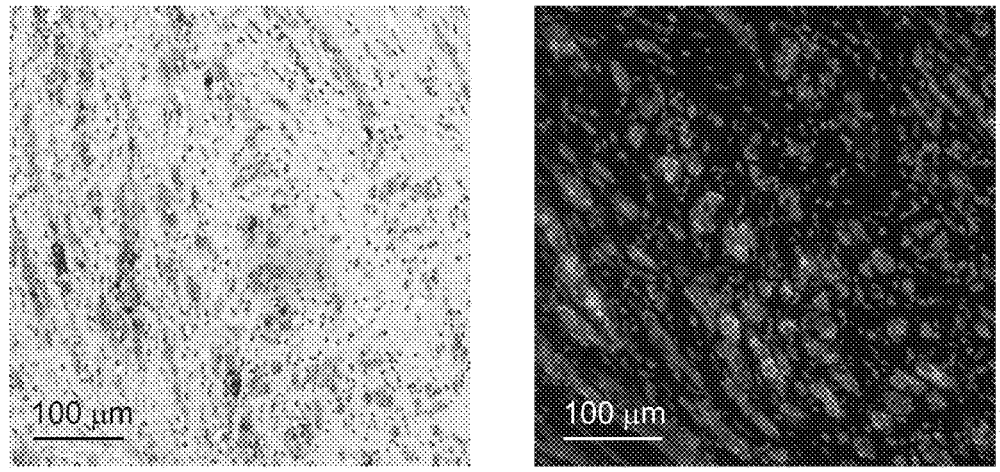
Figure 1D:
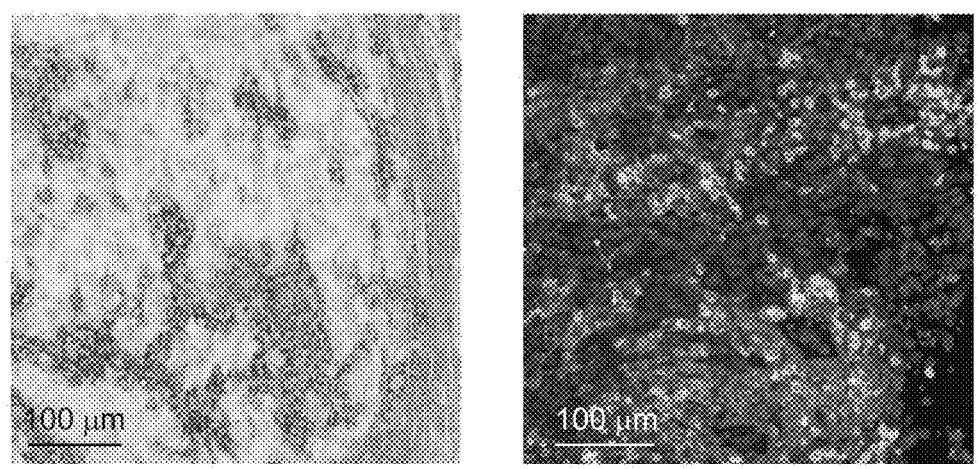
Figure 2A:
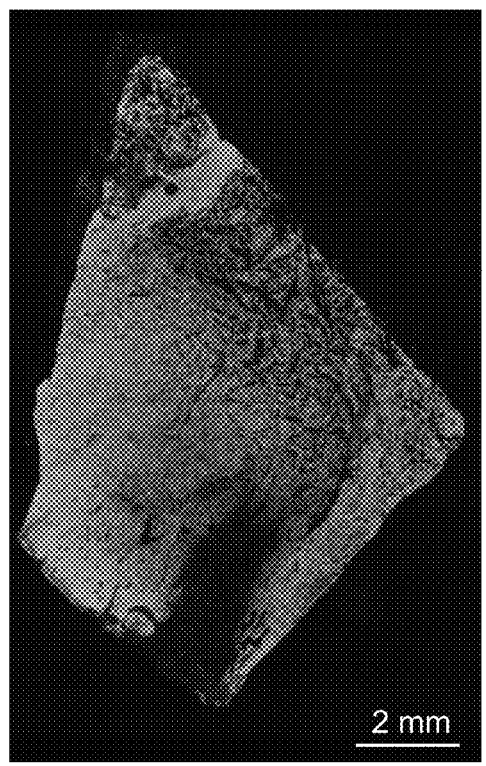
FIG. 2A shows a low magnification image of the tissue section that was immunohistochemically stained for PD-L1 expression and PD-1 expression in a multiparametric fluorescence IHC assay using an anti-PD1 antibody (green) and anti-PD-L1 mAb (red) and FIG. 2B shows the coordinates of 10,000 randomly sampled 2 pixel discs plotted in X, Y plane for this tissue section, which was selected as the region of interest (ROI) for proximity analysis.
Figure 2B:
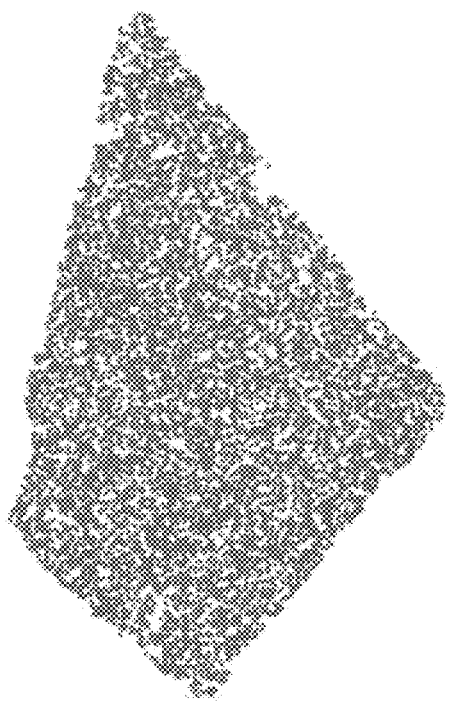

Throughout the detailed description and examples of the invention the following abbreviations will be used:
CDR Complementarity determining region
CHO Chinese hamster ovary
CR Complete Response
DAPI 4',6-diamidino-2-phenylindole
DFS Disease free survival
FFPE formalin-fixed, paraffin-embedded
FR Framework region
HRP Horseradish peroxidase
IgG Immunoglobulin G
IHC Immunohistochemistry or immunohistochemical
OR Overall response
OS Overall survival
PD Progressive Disease
PD-1 Programmed Death 1
PD-L1 Programmed Cell Death 1 Ligand 1
PD-L2 Programmed Cell Death 1 Ligand 2
PFS Progression free survival (PFS)
PR Partial Response
Q2W One dose every two weeks
Q3W One dose every three weeks
RECIST Response Evaluation Criteria in Solid Tumors
SD Stable Disease
VH Immunoglobulin heavy chain variable region
VK Immunoglobulin kappa light chain variable region I. Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"About" when used to modify a numerically defined parameter (e.g., the gene signature score for a gene signature discussed herein, or the dosage of a PD-1 antagonist, or the length of treatment time with a PD-1 antagonist) means that the parameter may vary by as much as 10% above or below the stated numerical value for that parameter. For example, a proximity threshold score of about 0.2% includes scores of 0.18%, 0.19%, 0.20%, 0.21% and 0.22%.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

"Biotherapeutic agent" means a biological molecule, such as an antibody or fusion protein, that blocks ligand/receptor signaling in any biological pathway that supports tumor maintenance and/or growth or suppresses the anti-tumor immune response.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Particularly preferred cancers that may be treated in accordance with the present invention include those characterized by elevated expression of one or both of PD-L1 and PD-L2 in tested tissue samples.

"CDR" or "CDRs" as used herein means complementarity determining region(s) in an immunoglobulin variable region, defined using the Kabat numbering system, unless otherwise indicated.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, anti-sense oligonucleotides that that inhibit expression of genes implicated in abnormal cell proliferation or tumor growth. Chemotherapeutic agents useful in the treatment methods of the present invention include cytostatic and/or cytotoxic agents.

"Clothia" as used herein means an antibody numbering system described in Al-Lazikani et al., *JMB* 273:927-948 (1997).

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |

TABLE 1-continued

Exemplary Conservative Amino Acid Substitutions

| Original residue | Conservative substitution |
|---|---|
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition.

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared ×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

"Patient" or "subject" refers to any single subject for which therapy is desired or that is participating in a clinical trial, epidemiological study or used as a control, including humans and mammalian veterinary patients such as cattle, horses, dogs, and cats.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the various aspects and embodiments of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the various aspects and embodiments of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful as PD-1 antagonists in the various aspects and embodiments of the present invention, are described in U.S. Pat. No. 7,521,051, U.S. Pat. No. 8,008,449, and U.S. Pat. No. 8,354,509. Specific anti-human PD-1 mAbs useful as the PD-1 antagonist in the various aspects and embodiments of the present invention include: MK-3475, a humanized IgG4 mAb with the structure described in *WHO Drug Information*, Vol. 27, No. 2, pages 161-162 (2013) and which comprises the heavy and light chain amino acid sequences shown in FIG. 14; nivolumab (BMS-936558), a human IgG4 mAb with the structure described in *WHO Drug Information*, Vol. 27, No. 1, pages 68-69 (2013) and which comprises the heavy and light chain amino acid sequences shown in FIG. 15; and the humanized antibodies h409A11, h409A16 and h409A17, which are described in WO2008/156712.

Examples of mAbs that bind to human PD-L1, and useful as PD-1 antagonists in any of the various aspects and embodiments of the present invention, are described in WO2013/019906, WO2010/077634 A1 and U.S. Pat. No. 8,383,796. Specific anti-human PD-L1 mAbs useful as the PD-1 antagonist in the various aspects and embodiments of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the various aspects and embodiments of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, compositions and uses of the present invention include AMP-224 (also known as B7-DCIg), which is a PD-L2-FC fusion protein and binds to human PD-1.

In some preferred embodiments of the various aspects of the present invention, the PD-1 antagonist is a monoclonal antibody, or antigen binding fragment thereof, which comprises: (a) light chain CDRs SEQ ID NOs: 1, 2 and 3 and heavy chain CDRs SEQ ID NOs: 4, 5 and 6; or (b) light chain CDRs SEQ ID NOs: 7, 8 and 9 and heavy chain CDRs SEQ ID NOs: 10, 11 and 12.

In other preferred embodiments of the various aspects of the present invention, the PD-1 antagonist is a monoclonal antibody, or antigen binding fragment thereof, which specifically binds to human PD-1 and comprises (a) a heavy chain variable region comprising SEQ ID NO:13 or a variant thereof, and (b) a light chain variable region comprising an amino acid sequence selected from the group consisting of SEQ ID NO:15 or a variant thereof; SEQ ID NO:16 or a variant thereof; and SEQ ID NO: 17 or a variant thereof. A variant of a heavy chain variable region sequence is identical to the reference sequence except having up to 17 conservative amino acid substitutions in the framework region (i.e., outside of the CDRs), and preferably has less than ten, nine, eight, seven, six or five conservative amino acid substitutions in the framework region. A variant of a light chain variable region sequence is identical to the reference sequence except having up to five conservative amino acid substitutions in the framework region (i.e., outside of the CDRs), and preferably has less than four, three or two conservative amino acid substitution in the framework region.

In another preferred embodiment of the various aspects of the present invention, the PD-1 antagonist is a monoclonal antibody which specifically binds to human PD-1 and comprises (a) a heavy chain comprising SEQ ID NO: 14 and (b) a light chain comprising SEQ ID NO:18, SEQ ID NO:19 or SEQ ID NO:20.

In yet another preferred embodiment of the aspects of the present invention, the PD-1 antagonist is a monoclonal antibody which specifically binds to human PD-1 and comprises (a) a heavy chain comprising SEQ ID NO: 14 and (b) a light chain comprising SEQ ID NO:18.

Table 2 below provides a list of the amino acid sequences of exemplary anti-PD-1 mAbs for use as PD-1 antagonists in the various aspects of the present invention of the present invention, and the sequences are shown in FIGS. 9-13.

TABLE 2

| Exemplary anti-human PD-1 antibodies |  |
|---|---|
| A. Comprises light and heavy chain CDRs of hPD-1.08A in WO2008/156712 | |
| CDRL1 | SEQ ID NO: 1 |
| CDRL2 | SEQ ID NO: 2 |
| CDRL3 | SEQ ID NO: 3 |
| CDRH1 | SEQ ID NO: 4 |
| CDRH2 | SEQ ID NO: 5 |
| CDRH3 | SEQ ID NO: 6 |
| B. Comprises light and heavy chain CDRs of hPD-1.09A in WO2008/156712 | |
| CDRL1 | SEQ ID NO: 7 |
| CDRL2 | SEQ ID NO: 8 |
| CDRL3 | SEQ ID NO: 9 |
| CDRH1 | SEQ ID NO: 10 |
| CDRH2 | SEQ ID NO: 11 |
| CDRH3 | SEQ ID NO: 12 |

TABLE 2-continued

| Exemplary anti-human PD-1 antibodies |  |
|---|---|
| C. Comprises the mature h109A heavy chain variable region and one of the mature K09A light chain variable regions in WO2008/156712 | |
| Heavy chain VR | SEQ ID NO: 13 |
| Light chain VR | SEQ ID NO: 15 or SEQ ID NO: 16 or SEQ ID NO: 17 |
| D. Comprises the mature 409 heavy chain and one of the mature K09A light chains in WO2008/156712 | |
| Heavy chain | SEQ ID NO: 14 |
| Light chain | SEQ ID NO: 18 or SEQ ID NO: 19 or SEQ ID NO: 20 |

"Primary anti-PD-1 antibody" refers to an antibody, or an antigen binding fragment thereof, that binds specifically to PD-1 in a tissue section, and is generally the first antibody used in an IHC assay to detect PD-1 positive cells in a tumor sample. In one embodiment, the primary antibody is the only antibody used to immunohistochemically stain a tumor sample for PD-1 expression. Preferably, the primary anti-PD-1 antibody is a monoclonal antibody.

Antibodies, which are useful as a primary anti-PD-1 antibody for IHC assay, should bind to the mature form of PD-1 (lacking the presecretory leader sequence, also referred to as leader peptide) that is expressed on the surface of certain mammalian cells. The terms "PD-1" and "mature PD-1" are used interchangeably herein, and shall be understood to mean the same molecule unless otherwise indicated or readily apparent from the context. As used herein, an anti-human PD-1 antibody or an anti-hPD-1 antibody refers to an antibody that specifically binds to mature human PD-1.

Examples of mAbs that are useful as a primary anti-hPD-1 antibody for IHC staining will produce essentially the same staining results on an FFPE or frozen tissue section of a tumor sample from a human as produced by NAT105, mouse anti-human PD-1 mAb available from Cell Marque.

"Primary anti-PD-Ligand antibody" refers to an antibody, or antigen binding fragment thereof, that binds specifically to one or both of PD-L1 and PD-L2 in a tissue section, and is generally the first antibody used in an IHC assay to detect PD-Ligand positive cells in a tumor sample. In one embodiment, the primary antibody is the only antibody used to immunohistochemically stain a tumor sample for expression of PD-Ligand, i.e., one or both of PD-L1 and PD-L2. Preferably, the primary anti-PD-L1 antibody is a monoclonal antibody.

Antibodies, which are useful as a primary anti-PD-L1 antibody for IHC assay, should bind to the mature form of PD-L1 (lacking the presecretory leader sequence, also referred to as leader peptide) that is expressed on the surface of certain mammalian cells. The terms "PD-L1" and "mature PD-L1" are used interchangeably herein, and shall be understood to mean the same molecule unless otherwise indicated or readily apparent from the context. As used herein, an anti-human PD-L1 antibody or an anti-hPD-L1 antibody refers to an antibody that specifically binds to mature human PD-L1.

Examples of mAbs that are useful as a primary anti-hPD-L1 antibody for IHC staining will produce essentially the same staining results on an FFPE or frozen tissue section of a tumor sample from a human as produced by Antibody 20C3 or Antibody 22C3. The amino acid sequences of the mature heavy and light chain variable regions for these antibodies are disclosed in application U.S. 61/807,581 filed 21 Dec. 2012.

For indirect IHC assay, the primary anti-PD-1 antibody and primary anti-PD-L1 antibodies are preferably raised in different species or engineered to have constant regions from different species. For example, in some embodiments of the present invention, when the primary anti-PD-1 mAb is a mouse antibody, a chimeric antibody comprising the Fab of the parental mouse 22C3 or mouse 20C3 and a rat constant region. One preferred chimeric anti-PD-L1 mAb that is useful as the primary anti-PD-L1 antibody comprises the mature heavy and light chains shown in FIG. 17.

"Secondary anti-PD-1 antibody" refers to an antibody that binds specifically to a primary anti-PD-1 antibody, thereby forming a bridge between the primary antibody and a subsequent detection reagent, if any. The secondary antibody is generally the second antibody used to immunohistochemically stain a tumor sample for PD-1 expression.

"Secondary anti-PD-Ligand antibody" refers to an antibody that binds specifically to a primary anti-PD-Ligand antibody, thereby forming a bridge between the primary antibody and a subsequent detection reagent, if any. The secondary antibody is generally the second antibody used to immunohistochemically stain a tumor sample for PD-Ligand expression.

"RECIST 1.1 Response Criteria" as used herein means the definitions set forth in Eisenhauer et al., E. A. et al., Eur. J Cancer 45:228-247 (2009) for target lesions or nontarget lesions, as appropriate based on the context in which response is being measured.

"Reference proximity score" or "Reference PD-1:PD-Ligand proximity score" as used herein means the PD-1:PD-Ligand proximity score that has been determined to divide at least the majority of responders from at least the majority of non-responders in a reference population of subjects who have the same tumor type as a test subject and who have been treated with a PD-1 antagonist. The PD-Ligand component of the score may be either or both of PD-L1 and PD-L2, and preferably is only PD-L1. Preferably, at least any of 60%, 70%, 80% or 90% of responders in the reference population will have a PD-1:PD-ligand proximity score that is above the selected reference score, while the a PD-1:PD-ligand proximity score for at least any of 60%, 70% 80%, 90% or 95% of the non-responders in the reference population will be lower than the selected reference proximity score. In some embodiments, the negative predictive value of the reference score is greater than the positive predictive value. In some preferred embodiments, responders in the reference population are defined as subjects who achieved a partial response (PR) or complete response (CR) as measured by RECIST 1.1 criteria and non-responders are defined as not achieving any RECIST 1.1 clinical response. In particularly preferred embodiments, subjects in the reference population were treated with substantially the same anti-PD-1 therapy as that being considered for the test subject, i.e., administration of the same PD-1 antagonist using the same or a substantially similar dosage regimen.

"Sample" when referring to a tumor or any other biological material referenced herein, means a sample that has been removed from the subject; thus, none of the testing methods described herein are performed in or on the subject.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5 or 3 times longer than the treatment duration.

"Tissue Section" refers to a single part or piece of a tissue sample, e.g., a thin slice of tissue cut from a sample of a normal tissue or of a tumor. Multiple adjacent sections of a single tissue sample may be prepared and analyzed in accordance with the present invention.

"Treat" or "treating" a cancer as used herein means to administer a PD-1 antagonist other therapeutic agent to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, J. Nucl. Med. 50:1S-10S (2009); Eisenhauer et al., supra). In some preferred embodiments, response to a PD-1 antagonist is assessed using RECIST 1.1 criteria. In some embodiments, the treatment achieved by a therapeutically effective amount is any of PR, CR, PFS, DFS, OR or OS. In some preferred embodiments, a proximity biomarker of the invention predicts whether a subject with a solid tumor is likely to achieve a PR or a CR. The dosage regimen of a therapy described herein that is effective to treat a cancer patient may vary according to factors such as the disease state, age, and weight of the patient, and the ability of the therapy to elicit an anti-cancer response in the subject. While an embodiment of the treatment method, medicaments and uses of the present invention may not be effective in achieving a positive therapeutic effect in every subject, it should do so in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Tumor tissue biomarker" as used herein refers to a protein, other than PD-1 or a PD-Ligand, which is expressed by neoplastic cells at much higher levels than by normal cells, and is capable of being detected by IHC assay.

Preferred tumor tissue biomarkers are proteins that are specific to a particular type of tumor, such as MART-1 and HMGB45 for melanoma. Examples of other tumor specific biomarkers include alpha fetoprotein for hepatocellular carcinoma, CD20 for B-cell lymphoma, CD3 for T-cell lymphoma, CD10 for renal cell carcinoma and acute lymphoblastic leukemia, CD15 and CD30 for Hodgkin's disease, carcinoembryonic antigen (CEA) for adenocarcinomas, EGFR (HER-1) for head and neck cancer, HER2/neu (ErbB2) for breast cancer, and various cytokeratins for tumors of epithelial origin.

"Variable regions" or "V region" as used herein means the segment of IgG chains which is variable in sequence between different antibodies. It extends to Kabat residue 109 in the light chain and 113 in the heavy chain.

II. Utility of Proximity Biomarkers of the Invention

A PD-1:PD-Ligand proximity biomarker described herein is useful to identify cancer patients who are most likely to achieve a clinical benefit from treatment with a PD-1 antagonist. This utility supports the use of these biomarkers in a variety of research and commercial applications, including but not limited to, clinical trials of PD-1 antagonists in which patients are selected on the basis of their proximity score, diagnostic methods and products for determining a patient's PD-1:PD-Ligand proximity score or for classifying a patient as positive or negative for a PD-1:PD-Ligand proximity biomarker, personalized treatment methods which involve tailoring a patient's drug therapy based on the patient's PD-1:PD-Ligand proximity score, as well as pharmaceutical compositions and drug products comprising a PD-1 antagonist for use in treating patients who test positive for a PD-1:PD-Ligand proximity biomarker.

The utility of any of the applications claimed herein does not require that 100% of the patients who test positive for a biomarker of the invention achieve an anti-tumor response to a PD-1 antagonist; nor does it require a diagnostic method to have a specific degree of specificity or sensitivity in determining the presence or absence of a biomarker in every subject, nor does it require that a diagnostic method claimed herein be 100% accurate in predicting for every subject whether the subject is likely to have a beneficial response to a PD-1 antagonist. Thus, the inventors herein intend that the terms "determine", "determining" and "predicting" should not be interpreted as requiring a definite or certain result; instead these terms should be construed as meaning either that a claimed method provides an accurate result for at least the majority of subjects or that the result or prediction for any given subject is more likely to be correct than incorrect.

Preferably, the accuracy of the result provided by a diagnostic method of the invention is one that a skilled artisan or regulatory authority would consider suitable for the particular application in which the method is used.

Similarly, the utility of the claimed drug products and treatment methods does not require that the claimed or desired effect is produced in every cancer patient; all that is required is that a clinical practitioner, when applying his or her professional judgment consistent with all applicable norms, decides that the chance of achieving the claimed effect of treating a given patient according to the claimed method or with the claimed composition or drug product.

A. Testing for Biomarkers of the Invention

A PD-1:PD-Ligand proximity score is determined for a sample of tumor tissue removed from a subject before and/or after exposure of the subject to one or more therapeutic agents, e.g. a PD-1 antagonist or a chemotherapeutic agent or another biotherapeutic agent. Accordingly, tumor samples may be removed from a subject over a period of time. The tumor may be primary or recurrent, and may be of any type (as described above), any stage (e.g., Stage I, II, III, or IV or an equivalent of other staging system), and/or histology. The subject may be of any age, gender, treatment history and/or extent and duration of remission.

The tumor sample can be obtained by a variety of procedures including, but not limited to, surgical excision, aspiration or biopsy. The tumor sample may be sectioned and assayed as a fresh tissue specimen; alternatively, the tumor sample may be frozen for further sectioning. In some preferred embodiments, the tumor sample is preserved by fixing and embedding in paraffin or the like.

The tumor sample may be fixed by conventional methodology, with the length of fixation depending on the size of the tissue sample and the fixative used. Neutral buffered formalin, glutaraldehyde, Bouin's and paraformaldehyde are nonlimiting examples of fixatives. In preferred embodiments, the tumor sample is fixed with formalin. In some embodiments, the fixed tumor sample is also embedded in paraffin to prepare an FFPE tissue sample.

Typically, the tumor sample is fixed and dehydrated through an ascending series of alcohols, infiltrated and embedded with paraffin or other sectioning media so that the sample may be sectioned. Alternatively, the tumor sample is first sectioned and then the individual sections are fixed.

In some preferred embodiments, the proximity score for a tumor is determined using FFPE tissue sections of about 3-4 millimeters, and preferably 4 micrometers, which are mounted and dried on a microscope slide and then immunohistochemically stained.

Immunohistochemistry

An IHC assay typically begins with antigen retrieval, which may vary in terms of reagents and methods. The antigen retrieval process may involve pressure cooking, protease treatment, microwaving, or heating histologic sections in baths of appropriate buffers, with the standard goal of unmasking antigens hidden by formalin crosslinks or other fixation. See, e.g., Leong et al. *Appl. Immnunohistochem.* 4(3):201 (1996).

Two general methods of IHC may be used; direct and indirect assays. In a direct IHC assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting. Other radionuclides include $^{99}Tc$, $^{90}Y$, $^{111}In$, $^{32}P$, $^{11}C$, $^{15}O$, $^{13}N$, $^{18}F$, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe.

(b) Colloidal gold particles.

(c) Fluorescent or chemilluminescent labels including, but not limited to, rare earth chelates (europium chelates), fluorescein and its derivatives, rhodamine and its derivatives, isothiocyanate, phycoerythrin, phycocyanin, allophycocyanin, o-phthaladehyde, fluorescamine, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, Texas Red, dansyl, Lissamine, umbelliferone, phycocrytherin, phycocyanin, or commercially available fluorophores such SPECTRUM ORANGE® and SPECTRUM GREEN® and/or derivatives of any one or more of the above. The fluorescent labels can be conjugated to the antibody using the techniques disclosed in *Current Protocols in Immunology*, supra, for example. Fluorescence can be quantified using a fluorimeter.

Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor.

Examples of enzymatic labels include luciferases (e.g. firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langbne & H. Van Vunakis), Academic press, New York, 73:147-166 (1981). Examples of Enzyme-Substrate Combinations are:

(i) Horseradish peroxidase (HRP) with hydrogen peroxidase as a substrate, wherein the hydrogen peroxidase oxidizes a dye precursor, such as, e.g., 3,3' diamino benzidine (DAB), which produces a brown end product; 3-amino-9-ethylcarbazole (AEC), which upon oxidation forms a rose-red end product; 4-chloro-1-napthol (CN), which precipitates as a blue end product; and p-Phenylenediamine dihydrochloride/pyrocatecol, which generates a blue-black product; orthophenylene diamine (OPD) and 3,3',5,5'-tetramethyl benzidine hydrochloride (TMB);

(ii) alkaline phosphatase (AP) and para-Nitrophenyl phosphate, naphthol AS-MX phosphate, Fast Red TR and Fast Blue BB, napthol AS-BI phosphate, napthol AS-TR phosphate, 5-bromo-4-chloro-3-indoxyl phosphate (BCIP), Fast Red LB, Fast Garnet GBC, Nitro Blue Tetrazolium (NBT), and iodonitrotetrazolium violet (INT); and (iii) β1-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980.

Any method known in the art for conjugating the antibody molecules to the various moieties may be employed, including those methods described by Hunter, et al., (1962) *Nature* 144:945; David, et al., (1974) *Biochemistry* 13:1014; Pain, et al., (1981) *J. Immunol. Meth.* 40:219; and Nygren, J., (1982) *Histochem. and Cytochem.* 30:407. Methods for conjugating antibodies are conventional and very well known in the art.

In some embodiments, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

After antigen retrieval and an optional blocking step, the tissue section is exposed to the desired primary antibody (e.g., anti-PD-1 or anti-PD-Ligand) for a sufficient period of time and under suitable conditions to allow the primary antibody to bind to the target protein in the tissue section. Appropriate conditions for achieving this can be determined by routine experimentation, with one example of suitable conditions described in Example 1 below. The slide is then washed to remove unbound and excess amounts of the primary antibody.

In some embodiments, the primary antibody is linked to a detectable label, such as paramagnetic ions, radioactive isotopes, fluorochromes, and NMR-detectable substances, and the slide is evaluated for PD-1 or PD-Ligand staining using the appropriate imaging apparatus.

In other embodiments, immune complexes between the target antigen (i.e., PD-1 or PD-Ligand) and the primary antibody may be detected using a second binding agent that is linked to a detectable label. The second binding agent is preferably a secondary antibody, which is applied to the slide at a concentration and for a period of time sufficient to allow the formation of secondary immune complexes. The slide is then typically washed to remove any non-specifically bound secondary antibody, and the label in the secondary immune complexes is detected.

The secondary antibody may be labeled using avidin, strepavidin or biotin, which is independently labeled with a detectable moiety, such as a fluorescent dye (stain), a luminescent dye or a non-fluorescent dye. In principle, any enzyme that can be conjugated to or can bind indirectly to the secondary antibody (e.g., via conjugated avidin, strepavidin, biotin) could be used. The enzyme employed can be, for example, alkaline phosphatase (AP), HRP, beta-gal actosidase and/or glucose oxidase. The enzyme can also be directed at catalyzing a luminescence reaction of a substrate, such as, but not limited to, luciferase and aequorin, having a substantially non-soluble reaction product capable of luminescing or of directing a second reaction of a second substrate, such as but not limited to, luciferine and ATP or coelenterazine and Ca.sup.++, having a luminescing product. Finally, a detection reagent is applied that includes a chromagen or a fluorescently tagged molecule to visualize the localization of the immune complexes.

The tissue section may also be counterstained to provide contrast to the PD-1 and PD-Ligand stain, or to identify morphological features of interest, such as cell membranes, nuclei and the like. Examples of nuclear counterstains frequently used in IHC are chromogenic stains, such as hematoxylin, nuclear fast red, methyl green, and flourescent stains, such as Hoechst stain, DAPI and propidium iodide. Examples of other counterstains include eosin, which can be used to stain cytoplasm, and fluorophore-tagged phalloidin, for staining actin cytoskeleton in cells.

The IHC assay may be performed using an automated pathology system, which may include automated staining (conventional stains, histochemical techniques, immunostainers); automated in situ hybridization systems; automatic slide preparation (coverslip, slide drying) and integrated slide and cassette labeling. See, e.g., Roja et al., Review of imaging solutions for integrated, quantitative immunohistochemistry in the Pathology daily practice, *Folia Histochemica et Cytobiologica*, (2009) 47 (3): 349-354.

In some embodiments, a tissue section of the subject's tumor sample is immunohistochemically stained for PD-1 and PD-Ligand using a multiplex assay substantially similar to the assay described in Example 1 below.

It will be understood by the skilled artisan that practicing the processes of the invention do not require direct detection of immunohistochemically stained PD-1 and PD-Ligand molecules. Instead, immunohistochemically staining the tissue section for a molecule that extensively co-localizes with PD-1 may provide a substantially equivalent measurement of the number of PD-1 positive cells in the tumor sample. Similarly, immunohistochemically staining the tissue section for a molecule that extensively co-localizes with the PD-Ligand of interest may provide a substantially equivalent measurement of the number of PD-Ligand positive cells in the tumor sample. Thus, it is intended that such equivalent means of detecting PD-1 positive cells and PD-Ligand positive cells are embraced by the terms "stained for PD-1 expression" and "stained for PD-L expression" unless otherwise clear from the context, e.g., the text specifically requires the use of a primary antibody that binds to PD-1 or the PD-Ligand of interest.

A preferred IHC assay employs the commercially available Dako EnVision™ FLEX detection system, which is intended for use together with a Dako Autostainer instrument (Dako, an Agilent Technologies Company, Glostrup, Denmark). These reagents can be used off the shelf for other autostainers or for manually-performed staining (not performed with an autostainer).

Imaging and Proximity Analysis

After completing the staining process, the stained slide is analyzed for proximity of PD-1+ cells and PD-Ligand+ cells, either by a human, e.g., a pathologist, or a computer programmed to distinguish between the detectable labels used to stain PD-1 and PD-Ligand molecules. The analysis may be performed directly by viewing the slide through a microscope at low, medium (10-20×) and high power (40-60×), and is preferably performed by viewing one or more high resolution images of the slide taken at low or medium power. Low or medium power is typically used to detect stained neoplastic cells (both within and outside of tumor nests) and staining of associated stroma in the entire tissue section. These staining patterns are useful in defining the ROI. Images taken at medium and high power may be used to examine individual tumor nests or other features of interest within the ROI if appropriate to increase the sensitivity of the analysis.

Digital images may be obtained by any suitable means, including digital microscopy and digital slide scanning, as well as digital storage databases. Examples of commercially available slide scanning devices that will convert whole glass slides into digital images include the Aperio® family of eSlide capture devices, including the ScanScope FL (Aperio, Vista, Calif.); the Omnyx™ VL4 and V:120 Scanners (Pittsburgh, Pa.); and the iScan HT and iScan Coreo scanners from Ventana Medical Systems (Tucson, Ariz.).

In some embodiments, the digital image is analyzed using an automated, digital pathology system or an immunofluorescence pathology system which includes a processor that is configured to carry out any of the embodiments of the proximity analysis described herein. Examples of commercially available image analysis software include: Matlab® with the Image Processing Toolbox™ by MathWorks (Natick Mass.); PRECISION Image Analysis Solution (Aperio, Vista, Calif.), ImagePro® from Media Cybernetics (Rockville, Md.); Metamorph® Microscopy Automation & Image Analysis Software from Molecular Devices (Sunnyvale, Calif.); and Columbus™ Image Data Storage and Analysis System from PerkinElmer (Waltham, Mass.). When automated systems are used to analyze a digital image, it should be understood that performing the proximity scoring process does not require the actual display of the image, which may be digitally manipulated and analyzed without display.

Once an image is obtained, one or more regions of interest (ROIs) are defined in the image for proximity analysis. When the defined ROIs are combined, they should include substantially all of the neoplastic cells and associated stroma that are visible in the image. The term "substantially all" in this context means at least 80%, 85%, 90%, 95% or more of the visible neoplastic cells.

ROIs may be defined by: (a) an operator, such as a pathologist, who relies on the operator's experience to determine the appropriate ROI(s) to assess for proximity; (b) an image processing system based on image characteristics; or (c) by an operator working in coordination with an image processing system. In some embodiments, the ROI is automatically defined to separate stained tumor tissue from background staining using models well-known in the art of automated image analysis of immunohistochemically stained tissue. For example, the intensity of the PD-1-specific and PD-Ligand-specific stains and detection of counterstained nuclei may be employed to designate stained tissue to include in the ROI. Also, the designation of tumor tissue can be facilitated by incorporating in the IHC assay a tumor-specific detection reagent with a detectable label that is different than the PD-1 or PD-L1 labels.

The number of ROIs to define to comprise substantially all of the neoplastic cells and associated stroma for an image of a particular tissue section will typically depend on the characteristics of the tissue section. For example, when almost all of the tissue section consists of tumor tissue (i.e., neoplastic cells and associated stroma), then the operator may determine that a single ROI is appropriate. However, if the tissue section has two or more widely dispersed tumor nests that display PD-1 and PD-Ligand stained cells, it may be physiologically more appropriate to define an ROI around the perimeter of each tumor nest.

Figure 6A:
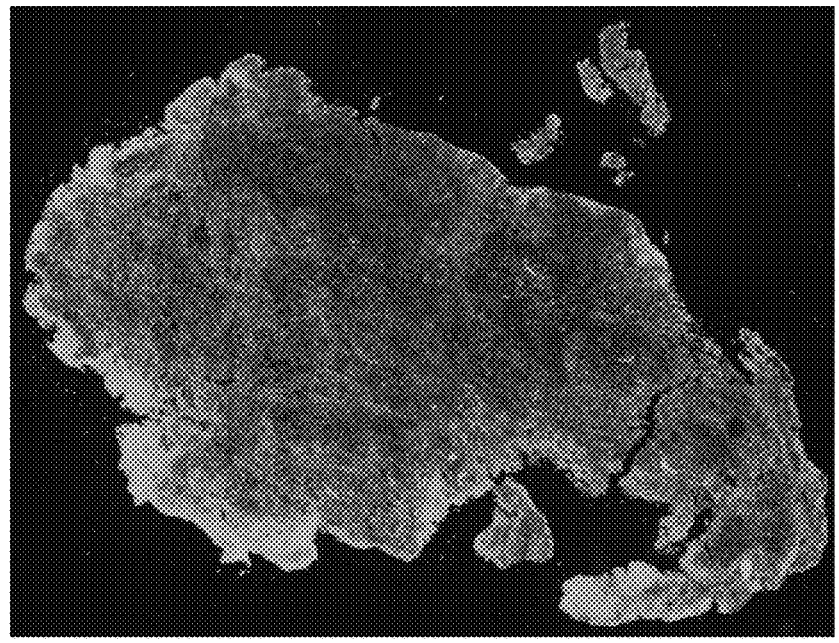
FIG. 6 illustrates the detection of three types of staining artifact observed in some FFPE tissue sections that have been immunohistochemically stained for PD-L1 expression and PD-1 expression by multiparametric fluorescence IHC assay using an anti-PD-1 antibody (green) and anti-PD-L1 mAb (red), with FIGS. 6A and 6B showing high intensity artifactual fluorescence seen around the edges of the tumor tissue in an image at low magnification (FIG. 6A) and high magnification (FIG. 6B), FIG. 6C showing low intensity auto fluorescence across the tissue in an image taken at low magnification, and FIGS. 6D and 6E showing images taken at low and high magnification of fluorescence generated by non-specific staining of blood, which fluoresces brightly in both the red and green channels.
Figure 6B:
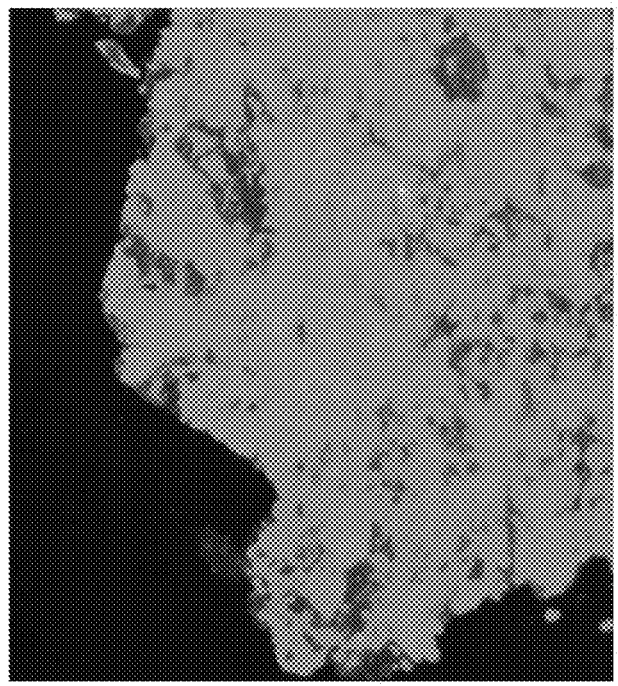
Figure 6C:
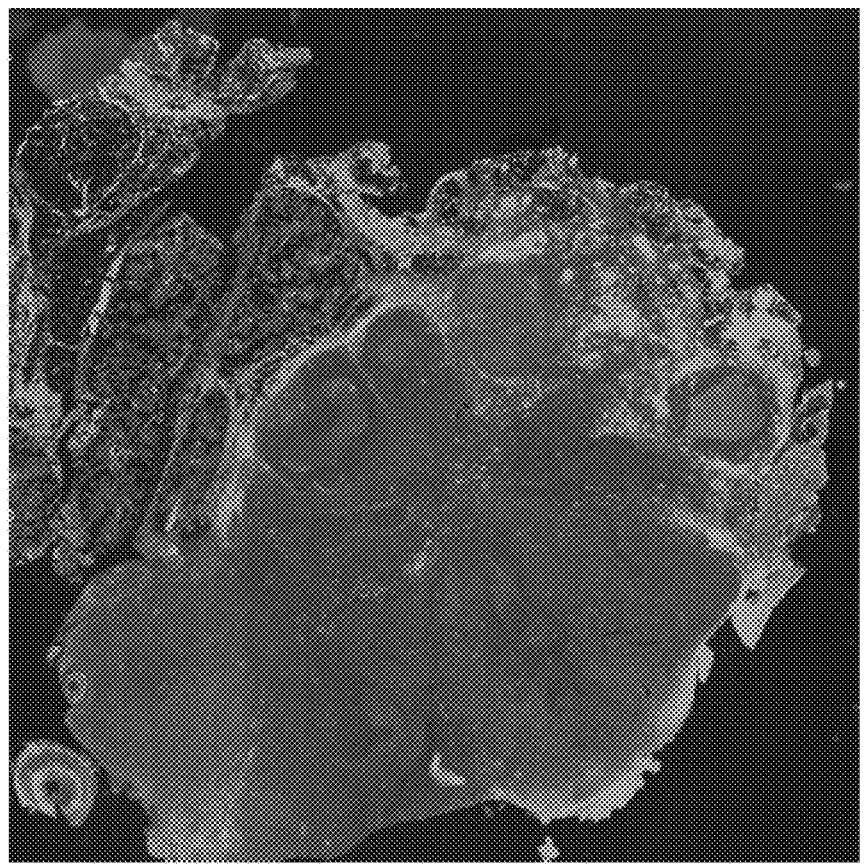
Figure 6D:
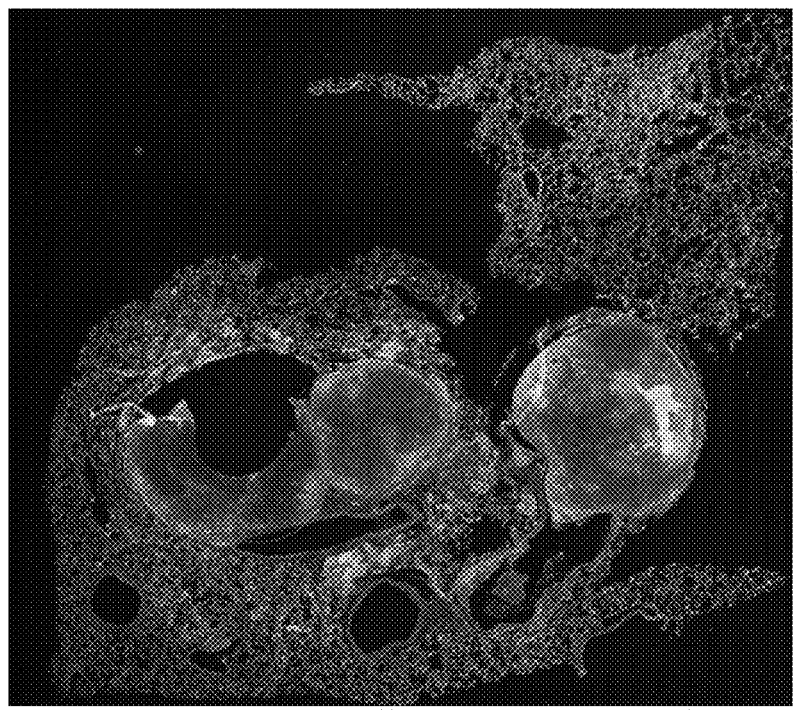
Figure 6E:
Figures 8A, 8B:
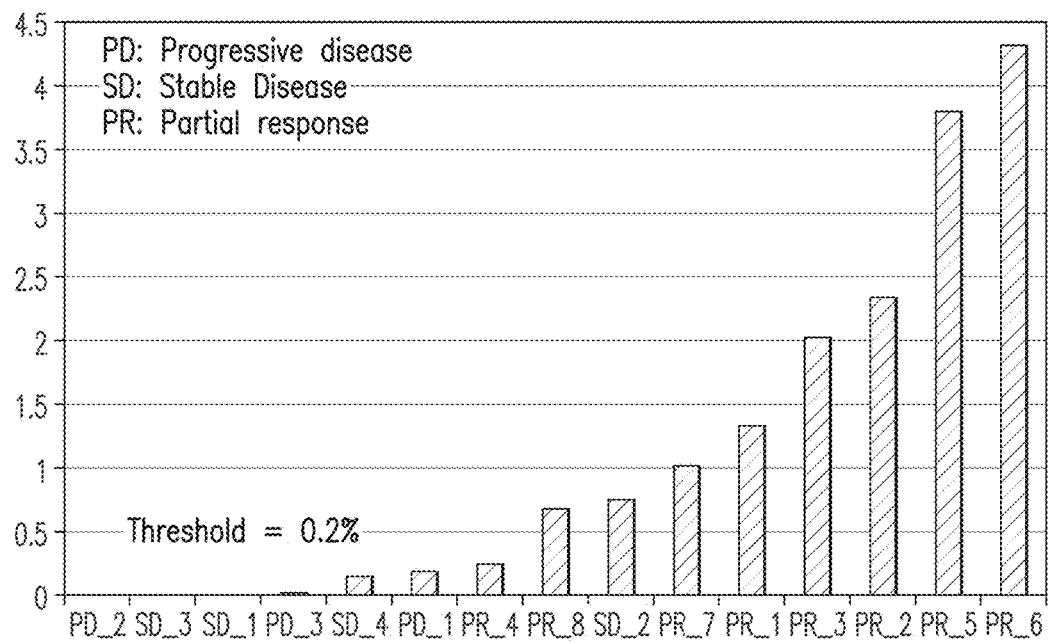
FIG. 8 illustrates the ability of a proximity assay of the invention using a threshold score of 0.2% to identify which patients in a cohort of 15 patients treated with MK-3475 were most likely to have an anti-tumor response, with FIG. 8A showing the proximity score determined for a pre-treatment tumor sample from each patient in the cohort and FIG. 8B showing a 2-Way Contingency Table of clinical response outcomes versus proximity biomarker assignments, i.e., negative or positive if the patient's proximity score was below or above the threshold score, respectively.

The invention also contemplates examining the image for staining artifacts and removing any artifacts that are identified. These artifact examination and removal steps may be performed prior to and/or after defining the ROI(s). Examples of such artifacts that may occur when the tissue is stained in a fluorescence IHC assay include a high intensity fluorescent signal observed around the edges of the tissues (e.g., see FIG. 6A), a low intensity autofluorescense signal observed across the tissue (e.g., see FIG. 6B) and a blood artifact that has the characteristics of contiguous large high intensity regions expressed in both PD1 and PDL1 channel compared to true PD1 and PDL1 signal which have honeycomb like structures (e.g., see FIG. 6C). If detected, the high intensity and low intensity artifacts may be removed from images by using the intensity distribution of individual channels that provide information for PD1 and PDL1 expression, and the blood artifact may be removed from images using both shape and intensity information.

After any artifacts are removed from a tissue section stained in a multiparametric fluorescence IHC assay, the ROI is preferably segmented to extract pixels that correspond to PD-1, PD-Ligand and tissue, and the segmentation results saved for the proximity analysis.

The ROI may be sampled for proximity analysis by randomly applying across the image of the ROI a series of points, which are used as the centers for generating subregions of the same, or substantially the same, shape and size. The shape of the subregion is not critical, e.g., it may be any nongeometric or geometric shape, including for example, a triangle, square, circle, pentagon, hexagon, and the like. The area covered by the subregion is preferably selected such that it captures physiologic interactions between a single PD-Ligand positive cell and a single PD-1 positive cell. For example, in some embodiments, a physiologically relevant area for a subregion is about the diameter of a lymphocyte, or about 7 micrometers. A suitable area size for a particular subregion shape will depend on various factors, e.g., the magnification of the image and the desired degree of discrimination between high and low numbers of spatially proximal cells, and may be empirically determined by the operator, e.g., a pathologist. For example, for disc shaped subregions and 200× image magnification, discs with radii in the range of 2-10 pixels will likely capture physiologic cell-cell interactions between PD-1 stained cells and PD-Ligand stained cells. The subregions should cover greater than at least 80%, 85%, 90% or 95% of the entire ROI, and the number of subregions to create is readily determined based on the size of the ROI, the coverage desired, and the shape and size of the subregion.

Each of the steps of obtaining a tumor sample, preparing a tissue section therefrom, immunohistochemically staining the tissue section, obtaining an image of the stained tissue section, and analyzing the image for proximity of PD-1+ cells and PD-L1+ cells may be performed by separate individuals at separate locations. For example, a surgeon may obtain by biopsy a tissue sample from a cancer patient's tumor and then send the tissue sample to a pathology lab, which may fix the tissue sample and then prepare one or more slides, each with a single tissue section, for the assay. The slide(s) may be stained by IHC soon after preparation, or stored for future staining. The same lab or a different lab may perform the IHC staining and obtain an image of the stained tissue section. The lab that produces the image of the IHC stained slide may conduct the proximity analysis, or alternatively provide the image to a person in another location to conduct the proximity analysis. A pathologist or trained professional who generates a proximity score may work for the diagnostic lab, or may be an independent contractor. Alternatively, a diagnostic lab may obtain a tumor sample from the subject's physician, or the surgeon who removed the tumor sample, and then perform all of the steps involved in sectioning the tumor sample, producing an immunohistochemically stained tissue section, generating an image and analyzing the image to assign a proximity score to the tissue section. It will be readily evident to the skilled artisan that other combinations of labs and trained operators may be utilized to perform all of the steps between obtaining a tumor sample and assigning a proximity score to the tumor sample.

In some embodiments, the individuals involved with preparing and assaying the tissue section for proximity of PD-1+ cells and PD-Ligand+ cells do not know the identity of the subject whose sample is being tested; i.e., the sample received by the laboratory is made anonymous in some manner before being sent to the laboratory. For example, the sample may be merely identified by a number or some other code (a "sample ID") and the results of the assay are reported to the party ordering the test using the sample ID. In preferred embodiments, the link between the identity of a subject and the subject's tissue sample is known only to the individual or to the individual's physician.

In some embodiments, after the test results have been obtained, the diagnostic laboratory generates a test report, which may comprise any one or both of the following results: the tissue sample was biomarker positive or negative, or the proximity score for the tumor sample and the reference proximity score for that tumor type.

In other embodiments, the test report may also include guidance on how to interpret the results for predicting if a subject is likely to respond to a PD-1 antagonist. For example, in one embodiment, the tested tumor sample has a proximity score at or above a pre-specified threshold, the test report may indicate that the subject has a score that is associated with response or better response to treatment with a PD-1 antagonist, while if the proximity score is below the threshold, then the test report indicates that the patient has a score that is associated with no response or poor response to treatment with a PD-1 antagonist. In some embodiments, the tested tissue section is from a melanoma tumor sample, the PD-Ligand is PD-L1 and the threshold PD-1:PD-Ligand proximity score is between 0.18% and 0.22%.

In some embodiments, the test report is a written document prepared by the diagnostic laboratory and sent to the patient or the patient's physician as a hard copy or via electronic mail. In other embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

Assigning a proximity score to a tissue section may be performed using a system that has been specially designed for this purpose. The system may include a kit that contains reagents for performing the multiparametric IHC assay on the tissue section and optionally hardware designed to scan and capture one or more images of the stained tissue section, and image analysis software that the operator may employ to analyze the image(s) for proximity.

B. Pharmaceutical Compositions, Drug Products and Treatment Regimens

In preferred embodiments, an individual to be treated by any of the methods and products described herein is a human subject diagnosed with a tumor, and a sample of the subject's tumor is available or obtainable to use for generating one or more tissue sections for conducting the PD-1:PD-Ligand proximity analysis.

The tumor tissue sample can be collected from a subject before and/or after exposure of the subject to one or more therapeutic treatment regimens, such as for example, a PD-1 antagonist, a chemotherapeutic agent, radiation therapy. Accordingly, tumor samples may be collected from a subject over a period of time. The tumor sample can be obtained by a variety of procedures including, but not limited to, surgical excision, aspiration or biopsy.

A physician may use a PD-1:PD-Ligand proximity biomarker as a guide in deciding how to treat a patient who has been diagnosed with a type of cancer that is known to be susceptible to treatment with a PD-1 antagonist or other chemotherapeutic agent(s). Prior to initiation of treatment with the PD-1 antagonist or the other chemotherapeutic agent(s), the physician would typically order a diagnostic test to determine if a tumor tissue sample removed from the patient is biomarker positive or negative. However, it is envisioned that the physician could order the first or subsequent diagnostic test at any time after the individual is administered the first dose of the PD-1 antagonist or other chemotherapeutic agent(s). In some embodiments, a physician may be considering whether to treat the patient with a pharmaceutical product that is indicated for patients whose tumor is biomarker positive. For example, if the reported PD-1:PD-Ligand proximity score is at or above a pre-specified threshold score that is associated with response or better response to treatment with a particular PD-1 antagonist, the patient is treated with a therapeutic regimen that includes at least the PD-1 antagonist (optionally in combination with one or more chemotherapeutic agents), and if the reported proximity score is below a pre-specified threshold score that is associated with no response or poor response to treatment with a PD-1 antagonist, the patient is treated with a therapeutic regimen that does not include any PD-1 antagonist.

In deciding how to use a proximity score or biomarker status in treating any individual patient, the physician may also take into account other relevant circumstances, such as the stage of the cancer, weight, gender, and general condition of the patient, including inputting a combination of these factors and the proximity score or biomarker status into a model that helps guide the physician in choosing a therapy and/or treatment regimen with that therapy.

The physician may choose to treat the patient who tests biomarker positive with a combination therapy regimen that includes a PD-1 antagonist and one or more additional therapeutic agents. The additional therapeutic agent may be, e.g., a chemotherapeutic, a biotherapeutic agent (including but not limited to antibodies to VEGF, EGFR, Her2/neu, VEGF receptors, other growth factor receptors, CD20, CD40, CD-40L, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33:183-186 (1994); dynemicin, including dynemicin A; bis-phosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy used to treat a biomarker positive patient may be administered either alone or in a medicament (also referred to herein as a pharmaceutical composition) which comprises the therapeutic agent and one or more pharmaceutically acceptable carriers, excipients and diluents, according to standard pharmaceutical practice.

Each therapeutic agent in a combination therapy used to treat a biomarker positive patient may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

Each chemotherapeutic agent in a combination therapy used to treat a biomarker positive patient can be administered orally or parenterally, including the intravenous, intramuscular, intraperitoneal, subcutaneous, rectal, topical, and transdermal routes of administration.

A patient may be administered a PD-1 antagonist prior to or following surgery to remove a tumor and may be used prior to, during or after radiation therapy.

In some embodiments, a PD-1 antagonist is administered to a patient who has not been previously treated with a biotherapeutic or chemotherapeutic agent, i.e., is treatment-naïve. In other embodiments, the PD-1 antagonist is administered to a patient who failed to achieve a sustained response after prior therapy with a biotherapeutic or chemotherapeutic agent, i.e., is treatment-experienced.

A therapy comprising a PD-1 antagonist is typically used to treat a tumor that is large enough to be found by palpation or by imaging techniques well known in the art, such as MRI, ultrasound, or CAT scan. In some preferred embodiments, the therapy is used to treat an advanced stage tumor having dimensions of at least about 200 mm$^3$, 300 mm$^3$, 400 mm$^3$, 500 mm$^3$, 750 mm$^3$, or up to 1000 mm$^3$.

Selecting a dosage regimen (also referred to herein as an administration regimen) for a therapy comprising a PD-1 antagonist depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of the PD-1 antagonist that is delivered to the patient consistent with an acceptable level of side effects. Accordingly, the dose amount and dosing frequency depends in part on the particular PD-1 antagonist, any other therapeutic agents to be used, and the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Biotherapeutic agents used in combination with a PD-1 antagonist may be administered by continuous infusion, or by doses at intervals of, e.g., daily, every other day, three times per week, or one time each week, two weeks, three weeks, monthly, bimonthly, etc. A total weekly dose is generally at least 0.05 mg/kg, 0.2 mg/kg, 0.5 mg/kg, 1 mg/kg, 10 mg/kg, 100 mg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144.

In some embodiments that employ an anti-human PD-1 mAb as the PD-1 antagonist, the dosing regimen will comprise administering the anti-human PD-1 mAb at a dose of 1, 2, 3, 5 or 10 mg/kg at intervals of about 14 days (±2 days) or about 21 days (±2 days) or about 30 days (±2 days) throughout the course of treatment.

In other embodiments that employ an anti-human PD-1 mAb as the PD-1 antagonist, the dosing regimen will comprise administering the anti-human PD-1 mAb at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In certain embodiments, a subject will be administered an intravenous (IV) infusion of a medicament comprising any of the PD-1 antagonists described herein, and such administration may be part of a treatment regimen employing the PD-1 antagonist as a monotherapy regimen or as part of a combination therapy.

In one preferred embodiment of the invention, the PD-1 antagonist is nivolumab, which is administered intravenously at a dose selected from the group consisting of: 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W.

In another preferred embodiment of the invention, the PD-1 antagonist is MK-3475, which is administered in a liquid medicament at a dose selected from the group consisting of 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W. In some particularly preferred embodiments, MK-3475 is administered as a liquid medicament which comprises 25 mg/ml MK-3475, 7% (w/v) sucrose, 0.02% (w/v) polysorbate 80 in 10 mM histidine buffer pH 5.5, and the selected dose of the medicament is administered by IV infusion over a time period of 30 minutes. The optimal dose for MK-3475 in combination with any other therapeutic agent may be identified by dose escalation starting with 2 mg/kg and going up to 10 mg/kg.

The present invention also provides a medicament which comprises a PD-1 antagonist as described above and a pharmaceutically acceptable excipient. When the PD-1 antagonist is a biotherapeutic agent, e.g., a mAb, the antagonist may be produced in CHO cells using conventional cell culture and recovery/purification technologies.

In some embodiments, a medicament comprising an anti-PD-1 antibody as the PD-1 antagonist may be provided as a liquid formulation or prepared by reconstituting a lyophilized powder with sterile water for injection prior to use. WO 2012/135408 describes the preparation of liquid and lyophilized medicaments comprising MK-3475 that are suitable for use in the present invention. In some preferred embodiments, a medicament comprising MK-3475 is provided in a glass vial which contains about 50 mg of MK-3475.

EXEMPLARY SPECIFIC EMBODIMENTS OF THE INVENTION

1. A process for assigning a PD-1:PD-Ligand proximity score to a tumor sample, which comprises:
    (a) obtaining an image of tissue that has been removed from the tumor sample and immunohistochemically stained for PD-1 and PD-Ligand expression in a manner that allows stained PD-1 cells to be distinguished from stained PD-Ligand cells;
    (b) defining in the image one or more regions of interest (ROIs) that comprises neoplastic cells and associated stroma, wherein substantially all of the neoplastic cells and associated stroma in the image are contained in the defined ROIs;
    (c) randomly creating across each defined ROI a plurality of subregions of substantially the same shape and size, wherein each of the subregions defines an area that is large enough to include a spatially proximal pair of a stained PD-1 cell and a stained PD-Ligand cell and small enough to exclude pairs of stained PD-1 and PD-Ligand cells that are not spatially proximal;
    (d) calculating the percent of all of the subregions that are positive for both stained PD-1 cells and stained PD-Ligand cells to generate the PD-1:PD-ligand proximity score for the tumor sample.

2. The process of embodiment 1, wherein the image represents the entirety of the stained tissue and only one ROI is defined for the image.

3. The process of embodiment 1, wherein the image represents the entirety of the stained tissue and two or more ROIs are defined for the image.

4. The process of any of the above embodiments, wherein defining the one or more ROIs comprises inspecting the image to identify neoplastic cells and associated stroma, and then applying a boundary to the image that surrounds the identified neoplastic cells and associated stroma.

5. The process of any of embodiments 1-3, wherein the tumor sample has been immunohistochemically stained for expression of a marker protein specific for the type of tumor comprising the tumor sample, and defining the one or more ROIs comprises applying to the image a boundary that mirrors the boundary of the tumor-specific staining 6. The process of any of the above embodiments, wherein the tissue has been immunohistochemically stained for the expression of both PD-L1 and PD-L2.

7. The process of any of embodiments 1 to 5, wherein the tissue has been immunohistochemically stained for the expression of only PD-L1.

8. The process of any of embodiments 1 to 5, wherein the tissue has been immunohistochemically stained for the expression of only PD-L2.

9. The process of any of the above embodiments, wherein the tissue has been counterstained with a nuclear stain.

10. The process of any of the above embodiments, wherein the image is obtained by a method comprising:
    (a) obtaining a tissue section from the tumor sample,
    (b) contacting the tissue section with an antibody specific for PD-1 (anti-PD-1 Ab) under conditions suitable for forming antibody-antigen complexes, and
    (c) washing the tissue section to remove unbound antibody and detecting antibody-antigen complexes comprising the PD-1 antibody,
    (d) contacting the tissue section with an antibody specific for PD-Ligand (anti-PD-Ligand Ab) under conditions suitable for forming antibody-antigen complexes, and
    (e) washing the tissue section to remove unbound antibody and detecting antibody-antigen complexes comprising the PD-Ligand antibody,
wherein steps (b) and (c) are performed before or after steps (d) and (e), or
wherein steps (b) and (d) are performed simultaneously and steps (c) and (e) are performed simultaneously.

11. The process of any of embodiments 1 to 9, wherein the image is obtained by a method comprising:
    (a) obtaining at least two adjacent tissue sections that have been stained in separate monoplex IHC assays, wherein one of the tissue sections has been stained for PD-1 using the anti-PD-1 Ab and the other tissue section has been stained for the PD-Ligand using the anti-PD-Ligand Ab,
    (b) creating a registered digital image of each of the stained tissue sections, and
    (c) superimposing the registered digital images to generate a composite image.

12. The process of embodiment 10 or 11, wherein the anti-PD-Ligand Ab is specific for PD-L1.

13. The process of embodiment 10 or 11, wherein the anti-PD-Ligand Ab is a bispecific antibody that binds both PD-L1 and PD-L2.

14. The process of any of the above embodiments, wherein the immunohistochemically stained tissue is obtained using a direct immunohistochemistry (IHC) assay.

15. The process of any of embodiments 1-13, wherein the immunohistochemically stained tissue is obtained using an indirect IHC assay.

16. The process of any of the above embodiments, wherein the PD-1 cells are stained with a first detectable label and the PD-Ligand cells are stained with a second detectable label that is distinguishable from the first label.

17. The process of embodiment 16, wherein the first and second detectable labels are first and second colors produced by fluorophores or chromogens.

18. The process of embodiment 16 or 17, wherein the image is a digital image and the process further comprises:

(a) segmenting the ROI to extract a first set of pixels for the first color and a second set of pixels for the second color, (b) assigning a positive value to each of the ROI subregions that has a pixel from each of the first and second extracted pixel sets, and (c) assigning a negative value to each of the ROI subregions that lacks a pixel from either of the first and second extracted pixel sets, wherein the segmenting step occurs prior to creating the subregions in the one or more ROIs.

19. The process of embodiment 18, which further comprises examining the image for fluorescing artifacts and removing any detected artifacts from the image, wherein the examining is performed prior to the segmenting step.

20. The process of embodiment 19, wherein the fluorescing artifacts comprise a low intensity autofluorescense signal across the tissue, a high intensity fluorescence around the edges of the tissue, and a blood artifact that manifests as a yellow color when red and green channels are combined due to bright fluorescence in both channels concurrently.

21. A process for testing a tumor sample for the presence or absence of a PD-1:PD-Ligand proximity biomarker that is predictive of an anti-tumor response to treatment with a PD-1 antagonist, which comprises:

(a) obtaining a PD-1:PD-Ligand proximity score for the tumor sample, (b) comparing the PD-1:PD-Ligand proximity score for the tumor sample with a threshold PD-1:PD-Ligand proximity score and (c) classifying the tumor as biomarker positive or biomarker negative, wherein if the proximity score for the tumor sample is equal to or greater than the threshold proximity score, then the tumor is classified as positive for the PD-1:PD-Ligand proximity biomarker, and if the obtained score is less than the threshold score, then the tumor is classified as negative for the PD-1:PD-Ligand proximity biomarker.

22. The process of embodiment 21, wherein each of the tumor sample and threshold proximity scores are obtained using the process of any of embodiments 1 to 20.

23. The process of embodiment 22, wherein the tumor sample is from a patient diagnosed with melanoma, the PD-Ligand is PD-L1 and the threshold proximity score is about 0.2%.

24. A method for treating a human patient having a tumor which comprises determining if the tumor is positive or negative for a PD-1:PD-Ligand proximity biomarker and administering to the subject a PD-1 antagonist if the tumor is positive for the biomarker and administering to the subject a cancer treatment that does not include a PD-1 antagonist if the tumor is negative for the biomarker.

25. The method of embodiment 24, wherein the determining step comprises obtaining a tumor sample from the patient, sending the tumor sample to a diagnostic laboratory, and receiving from the diagnostic laboratory a report that states whether the tumor sample is positive or negative for the biomarker.

26. A pharmaceutical composition comprising a PD-1 antagonist for use in a subject who has a tumor that tests positive for a PD-1:PD-Ligand proximity biomarker.

27. A drug product which comprises a pharmaceutical composition and prescribing information, wherein pharmaceutical composition comprises a PD-1 antagonist and at least one pharmaceutically acceptable excipient and the prescribing information states that the pharmaceutical composition is indicated for use in a subject who has a tumor that tests positive for a PD-1:PD-Ligand proximity biomarker.

28. The composition or drug product of embodiments 26 and 27, wherein the PD-1 antagonist is a monoclonal antibody that inhibits the binding of PD-L1 to PD-1.

29. The composition or drug product of embodiment 26 and 27, wherein the PD-1 antagonist is a monoclonal antibody that inhibits the binding of PD-L1 and PD-L2 to PD-1.

30. The composition or drug product of 29, wherein the PD-1 antagonist is MK-3475 or nivolumab.

31. The process, method, composition or drug product of any of the above embodiments, wherein the PD-1:PD-Ligand proximity score is obtained using the process of any of embodiments 1 to 20.

32. The process, method, composition or drug product of any of the above embodiments, wherein the tumor sample is from a human diagnosed with bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC) or triple negative breast cancer.

32. The process, method, composition or drug product of any of the above embodiments, wherein the tumor sample is from a human diagnosed with acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

33. The process, method, composition or drug product of any of embodiments 1 to 31, wherein the tumor sample is from a human diagnosed with ipilimumab-naïve advanced melanoma, ipilimumab-refractory advanced melanoma or NSCLC, and the PD-Ligand is PD-L1.

34. The process, method, composition or drug product of any of embodiments 1 to 31, wherein the tumor sample is from a human diagnosed with metastatic melanoma, the PD-1 antagonist is MK-3475, the PD-Ligand is PD-L1 and the threshold PD-1:PD-Ligand proximity score is about 0.2%.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$* ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausubel, et al. (2001) *Current Protocols in*

*Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Purification of antigen is not necessary for the generation of antibodies. Animals can be immunized with cells bearing the antigen of interest. Splenocytes can then be isolated from the immunized animals, and the splenocytes can be fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002)*J. Immunol.* 168:883-889).

Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLES

Example 1. Multiplex IHC Assay for PD-1 and PD-L1 Expression in FFPE Tumor Tissue Sections This example describes the process used to stain tumor samples for PD-1 and PD-L1 expression that were then imaged and assayed for proximity as discussed in the Examples below.

Reagents

| Description | Company | Catalog # | Working Conc. |
|---|---|---|---|
| Mouse anti-human PD-L1 mAb (Clone 22C3) | In house | N/A | 2 ug/mL |
| Envision Flex Mini Kit, High pH | Dako | K8023 | N/A |
| Envision FLEX + Mouse (LINKER) | Dako | K8022 | Ready to Use (RTU) |
| Normal Donkey Serum | Jackson | 017-000-121 | 3 mg/mL 5% by volume |
| Goat anti-human PD-1 polyclonal Ab | R&D | AF1086 | 2 ug/mL |
| Donkey anti-goat (biotinylated) IgG | Jackson | 705-065-147 | 6.5 ug/mL |
| ABC Elite | Vector | PK7100 | RTU |
| TSA Kit #4 with Alexa Fluor 568 tyramide | Invitrogen | T-20914 | See TSA prep |
| TSA Kit #2 with Alexa Fluor 488 tyramide | Invitrogen | T-20912 | See TSA prep |
| Antibody Diluent | Dako | S0809 | RTU |
| Mayer's Hematoxylin | Poly Scientific | S216-1GL | RTU |
| Micromount | Leica | 3801731 | RTU |

Preparation of Working Reagents from TSA Kit

Tyramide Stock Solution:

Dissolved component A into 150 uL of component B (provided DMSO). Mixed well and stored unused portions of this stock in 10 ul aliquots at <−20C with desiccant. Protected from light.

Prepared Amplification Buffer/0.15% H2O2 Intermediate Dilution:

Added 1 uL of component F (provided 30% hydrogen peroxide) to 200 uL of component E (provided amplification buffer) as intermediate dilution (0.15% H2O2), and diluted 1:100 of intermediate dilution into component E as working solution (freshly made before use). Final concentration of H2O2 is 0.0015%.

Working Alexa Fluor 568 and Alexa Fluor 488 TSA Solutions:

Prepared AF568 and AF488 tyramide each by diluting the stock solution 1:100 in amplification buffer/0.0015% H2O2.

Staining Protocol

Slides were freshly cut or stored at 4° C. until use.

On the day of use, slides were slides were baked at 60° C. for 45 minutes, and then deparaffinized on the Leica autostainer through 4 changes of xylene, 2 changes of 100% alcohol, 2 changes of 95% alcohol, 1 change of 70% alcohol, and 1 change of running deionized water.

After deparaffinization, antigens were retrieved by immersing the slides into Flex TRS (high pH) and allowing the temperature inside the PT Link to reach 97° C. for 20 minutes. Once this time elapsed, the chamber temperature was cooled to 75° C. Slides were removed from the PT Link and cooled to room temperature in Flex wash buffer.

Autostainer Program: Slides were loaded into the Dako autostainer which was programmed as follows:

| Step | Incubation Time (Minutes) | Rinses |
| --- | --- | --- |
| Envision Flex Peroxidase Block | 5 | 1x Envision Flex Buffer |
| Anti-PD-L1 mAb | 60 | 1x Envision Flex Buffer |
| Envision Flex+ Mouse Linker | 15 | 1x Envision Flex Buffer |
| Envision Flex/HRP | 20 | 1x Envision Flex Buffer |
| Alexa Fluor 568 TSA | 20 | 2x Deionized Water |
| | | 1x Envision Flex Buffer |
| 0.5N HCl | 3 | 1x Envision Flex Buffer |
| 5% Normal Donkey Serum | 15 | 1x Envision Flex Buffer |
| Anti-PD-1 polyclonal Ab | 60 | 1x Envision Flex Buffer |
| Donkey x Goat IgG Biotin | 30 | 1x Envision Flex Buffer |
| ABC Elite | 30 | 1x Envision Flex Buffer |
| Alexa Fluor 488 TSA | 5 | 2x Deionized Water |

After the autostainer program was complete, slides were removed from machine, immersed in deionized water, coverslipped with Vector Hardset Mounting media with DAPI and allowed to sufficiently dry before viewing on fluorescent microscope.

Example 2. Multicolor Immunohistochemistry of Tumor (Melanoma) Samples Demonstrates Distinct Spatial Patterns of PD-1 and PD-L1 Distribution in Archival FFPE Melanoma Samples Single parameter chromogenic immunohistochemical staining was performed using a mouse monoclonal anti-PD-L1 antibody (clone 22C3) and the brown DAB chromogen (FIG. 1, left column) Multiparametric fluorescence immunohistochemistry was performed using the protocol detailed in Example 1. In brief, formalin-fixed paraffin-embedded sections were stained using an anti-PD1 antibody (polyclonal goat anti-hPD-1, green) and an anti-PD-L1 antibody (clone 22C3, red). Representative patterns of PD-1 and PD-L1 are depicted in the images in the right-hand column. In contrast to the single parameter chromogenic stain, which is limited to demonstrating the range of PD-L1 expression per se, the dual fluorescence staining reveals distinct patterns of PD-L1 expression in relation to PD-1+ cells. PD-L1 can be identified as being either (1) spatially apart from PD-1+ T cells (A, right); (2) associated with a minimal PD-1+ infiltrate (B, right); (3) expressed in the absence of concomitant PD-1+ T cells (C, right); or (4) strongly expressed in tight spatial proximity to PD-1+CD8 T cells (D, right). These data suggest that the spatial proximity of PD-L1 (red) to PD1 (green) will be more predictive than PD-L1 expression of response to PD-1 antagonists.

Example 3. Random Disc Sampling of Tissue Sections for Quantifying PD-1 Expressing Cells and PD-L1 Expressing Cells in Spatial Proximity Multiparametric immunofluorescent immunohistochemistry was performed using the protocol detailed in Example 1. In brief, formalin-fixed paraffin-embedded sections were stained using an anti-PD1 antibody (green) and an anti-PD-L1 antibody (red). The slides were scanned using an Aperio ScanScope FL scanner (20x objective) and captured as afi fused sys files. The images were analyzed for staining artifacts such as the three fluorescent artifacts shown in FIG. 6. If found these artifacts were removed by the intensity distribution of individual channels that correspond to red pixels and green pixels and removed high intensity artifactual fluorescence around the edges of the stained tissue, low intensity artifactual fluorescence across the stained tissue, and used both shape and intensity information to remove the blood artifact. Once these artifacts were removed, the images were segmented to extract green and red pixels representing PD-1 and PD-L1 molecules, respectively, and the resulting segmentation was saved.

Figure 3A:
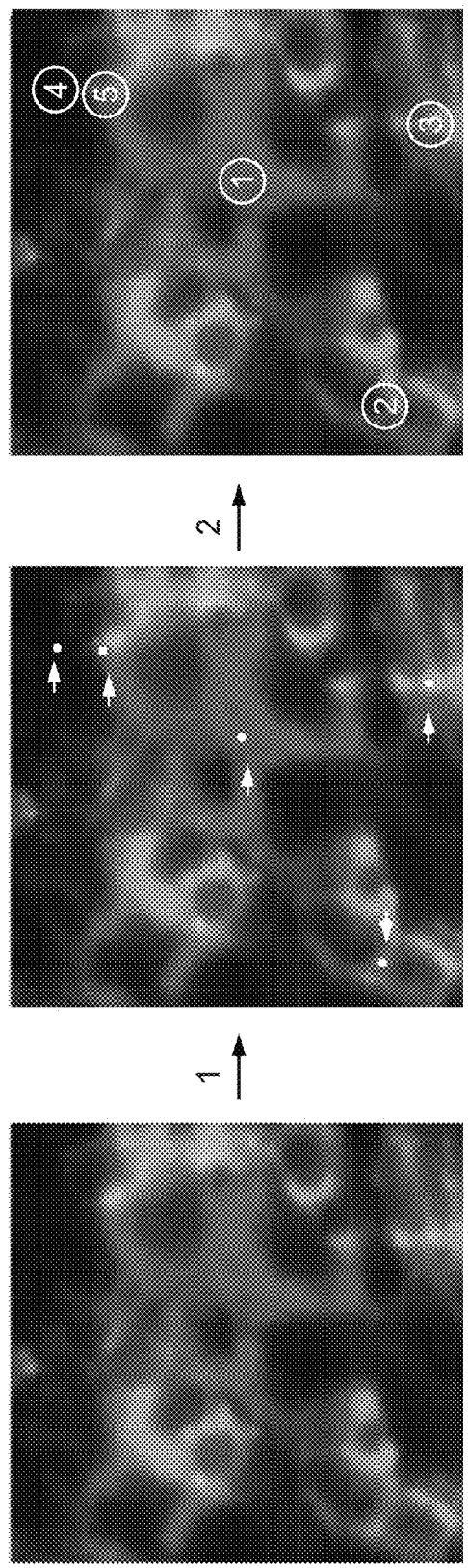
FIG. 3 illustrates the process of assigning a PD-1:PD-Ligand proximity score to a melanoma tumor sample in accordance with one embodiment of the invention, with FIG. 3A showing three panels of an image at high magnification of an FFPE tissue section that was sectioned from the tumor sample and then immunohistochemically stained for PD-L1 expression and PD-1 expression in a multiparametric fluorescence IHC assay using an anti-PD-1 antibody (green) and anti-PD-L1 mAb (red), with the left panel showing a portion of the ROI that was defined for analysis, the middle panel showing points randomly applied to the image, and the right panel showing 2 pixel radius discs that were centered on the randomly applied points, and FIG. 3B showing the results of analyzing the randomly created discs in FIG. 3A for positive or negative proximity of PD-1+ cells and PD-L1+ cells based on detecting the presence of both green and red pixels within each disc.
Figure 4A:
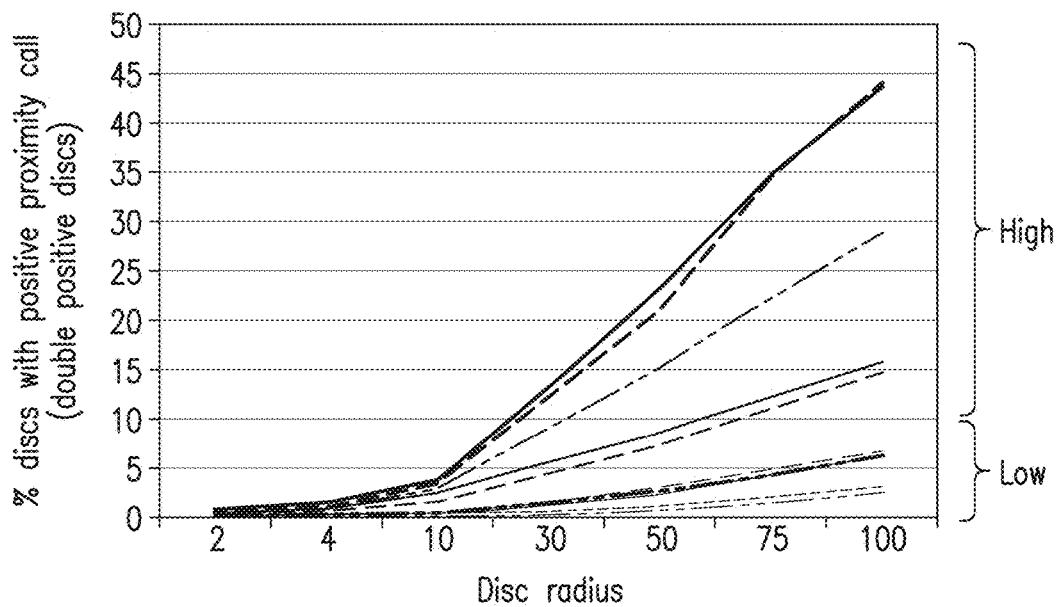
FIG. 4 illustrates the effect of the area size for 10,000 randomly created disc subregions on the ability of the proximity assay to discriminate between images of 10 melanoma tumor samples that had been determined by a pathologist to have high or low spatial proximity of PD-1+ cells and PD-L1+ cells, with FIG. 4A showing the data as percent of double positive discs at progressively increasing disc radii on a 0 to 50% scale and FIG. 4B showing the same data on a 0 to 1% scale.
Figure 4B:
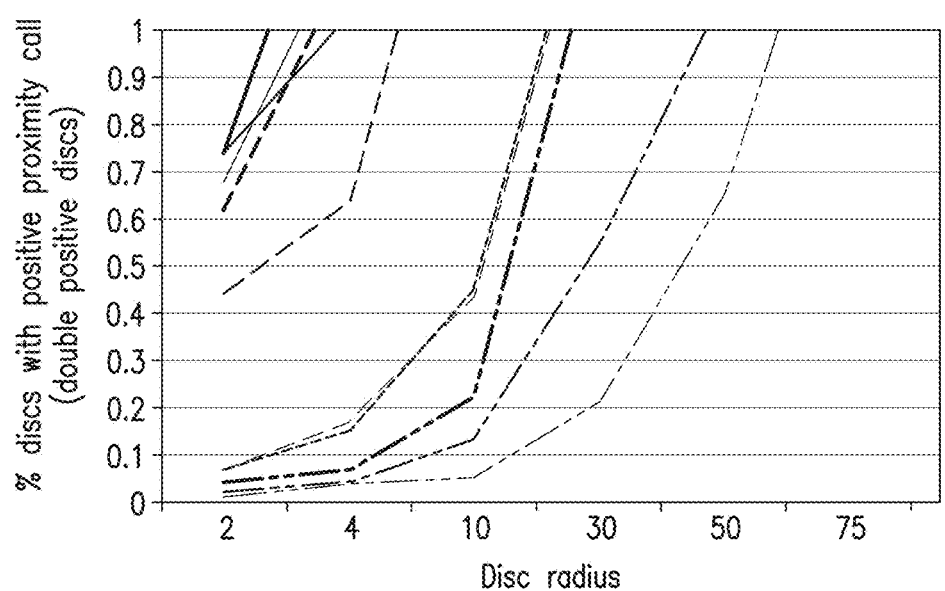

As illustrated in the digital image seen in FIG. 3A, left panel, each ROI generated on an image was analyzed by a random disc sampling methodology in which a large series of points was randomly applied to the image (FIG. 3A, middle panel), and then a disc with a radius of 2 pixels was centered around each of the randomly generated points (FIG. 3A, right panel, labeled 1-5). The number of red pixels and green pixels, representing PD-L1+ cells and PD-1+ cells, respectively, that were contained within each disc was calculated. Co-occurrence of at least one pixel of red and one pixel of green within a disc was given a proximity call of "positive", while any disc that did not contain at least one pixel of red and one pixel of green was given a proximity call of negative. As shown in FIG. 3B, the ROI examined in FIG. 3A was found to have 3 negative discs and 2 positive discs.

Example 4. Quantitative Proximity Analysis can Discriminate Between Tumors with High and Low Spatial Association of PD-L1 with PD-1

A test set of images (200x magnification) of melanoma tissue sections was selected by a pathologist to include 5 cases exhibiting abundant PD-1 in close spatial proximity to PD-L1 and 5 cases exhibiting minimal PD-1 in close spatial proximity to PD-1. In this analysis, 10,000 discs were used to randomly sample the images at progressively increasing disc radii, including radii of 2, 4, 10, 30, 50, 75 and 100 pixels. Although the separation between low and high proximity groups is retained across the range of disc sizes tested, the ability to discriminate between the two groups (measured as the ratio of the median high/median low) is maximal at a radius of 2 pixels. The ratio of median high/median low for the entire range of radii tested are as follows: 17 (2 pixel), 14 (4 pixel), 11 (10 pixel), 7 (30 pixel), 6 (50 pixel), 5 (75 pixel) and 5 (100 pixel). At 200× image magnification, the length of 1 pixel equals 0.494 microns. These results indicate that discs with pixel radii in the range of 2-10 will be appropriate to capture PD-1 positive cells and PD-L1 cells in physiologically relevant spatial proximity.

Figure 5:
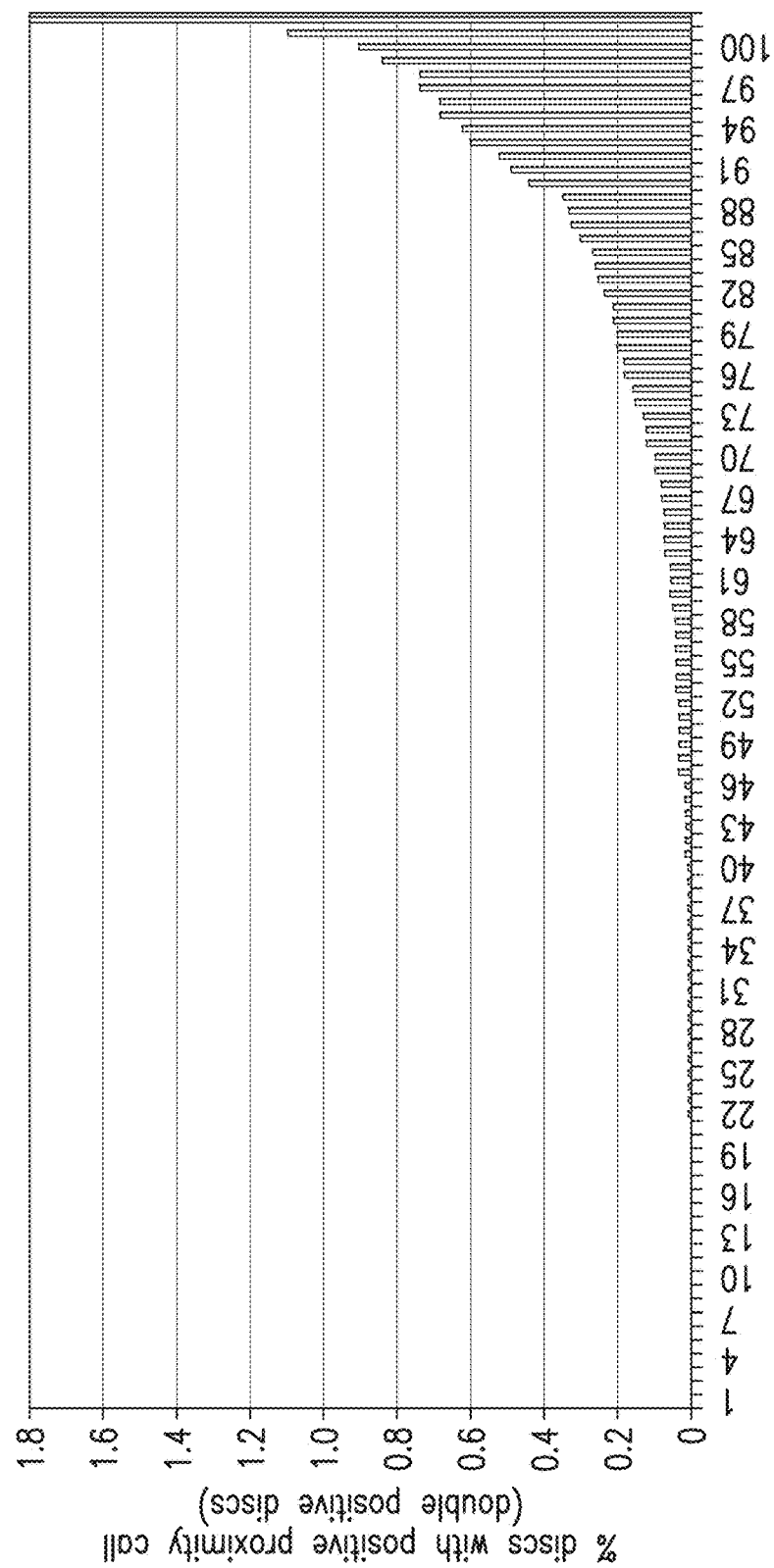
FIG. 5 shows a graph of the PD-1:PD-Ligand proximity scores (Y-axis) assigned to images of FFPE tissue sections from 102 individual melanoma tumor samples (X-axis) that had been subjected to a multiparametric fluorescence IHC assay and scored for proximity by determining the percentage of double-positive discs in 10,000 two-pixel radius discs that were randomly sampled across each image.

Example 5. Quantitative Proximity Analysis Yields a Continuous Variable Output which can be Used to Describe and Rank Human Tumor Samples A set of archived FFPE tissue sections from 102 melanoma patients were immunohistochemically stained for PD-1 and PD-L1 expression as described in Example 1, and images of the stained tissue sections were then analyzed using the random disc sampling method described in Examples 2-4. In brief, each image was analyzed for fluorescent artifacts and any artifacts detected were removed, the image was sectioned to extract red and green pixels, and then 10,000 2 pixel radius discs were randomly generated across the image. Discs were called proximity positive if the sampled disc contained at least 1 pixel of red and 1 of green. Discs that contained only red, only green, or neither red nor green pixels were designated as negative. FIG. 5 shows the results of the percent of discs for each individual melanoma case that was proximity positive (Y-axis) and demonstrates that this set of archival melanoma tissue sample has a wide distribution of PD-1:PD-Ligand proximity scores.

Example 6. Determination of Clinically Relevant Threshold for Discriminating Cases with "High" Versus "Low" Proximity Scores The proximity analysis data provided in FIG. 5 was re-plotted to show the cumulative percent of archival melanomas in which the proximity score exceeds each of a set of progressively increasing binary cut-points (i.e. thresholds) and the results are shown in FIG. 7. Along the X-axis are pre-defined thresholds as determined by percent double positive discs. Along the Y-axis is the percent of melanomas in the evaluated archival set that would fall above the threshold as defined, thus yielding a "positive" or "high" proximity value at that threshold. As shown in FIG. 7, the percentage of melanoma cases falling above each given proximity threshold increases as the threshold itself decreases. Proximity thresholds in the range of 0.05-0.3% double positive discs yield percent "positive" rates in tested archival melanomas that are similar to clinical response rates observed for melanoma cohorts treated with investigational anti-PD-1 mAbs. Based on this analysis of 102 archival melanomas, a threshold of 0.2% was selected as a useful parameter for subsequent analysis to determine whether quantitative proximity analysis can predict response and non-response to therapy with MK-3475.

Example 7. Proximity Analysis of Archival Melanoma Samples from Patients Treated with MK-3475 Discriminates Between Responders and Non-Responders FFPE melanoma samples obtained from fifteen patients prior to treatment with a PD-1 antagonist (MK-3475) were immunohistochemically stained for PD-1 and PD-L1 expression using the multiplex IHC assay described in Example 1, images were taken of the stained tissue sections and then the images were analyzed to assign a PD-1:PD-L1 proximity score as described in Examples 2-5. The proximity scores and response data for each individual melanoma case is shown in FIG. 7A. The assigned proximity scores were then compared with the 0.2% threshold selected in Example 6, to partition the 15 cases into negative/low proximity (<0.2% double-positive discs) and positive/high proximity (>0.2% double-positive discs) cases. A 2-Way Contingency Table was constructed (FIG. 7B) and analyzed using a Chi-Square Test, demonstrating a non-random segregation (Chi-Square=8.136) with a corresponding p-value of 0.004 (Yates corrected). The positive predictive value of a high proximity score was 0.889 whereas the negative predictive value for a low proximity score was 1.000.

A brief description of the sequences in the sequence listing is the table below:

| SEQ ID NO: | Description |
|---|---|
| 1 | hPD-1.08A light chain CDR1 |
| 2 | hPD-1.08A light chain CDR2 |
| 3 | hPD-1-08A light chain CDR3 |
| 4 | hPD-1.08A heavy chain CDR1 |
| 5 | hPD-1.08A heavy chain CDR2 |
| 6 | hPD-1.08A heavy chain CDR3 |
| 7 | hPD-1.09A light chain CDR1 |
| 8 | hPD-1.09A light chain CDR2 |
| 9 | hPD-1.09A light chain CDR3 |
| 10 | hPD-1.09A heavy chain CDR1 |
| 11 | hPD-1.09A heavy chain CDR2 |
| 12 | hPD-1.09A heavy chain CDR3 |
| 13 | 109A-H heavy chain variable region |
| 14 | 409A-H heavy chain full length |
| 15 | K09A-L-11 light chain variable region |
| 16 | K09A-L-16 light chain variable region |
| 17 | K09A-L-17 light chain variable region |
| 18 | K09A-L-11 light chain full length |
| 19 | K09A-L-16 light chain full length |
| 20 | K09A-L-17 light chain full length |
| 21 | MK-3475 Heavy chain |
| 22 | MK-3475 Light chain |
| 23 | Nivolumab Heavy chain |
| 24 | Nivolumab light chain |
| 25 | Antibody 22C3 heavy chain |
| 26 | Antibody 22C3 light chain |
| 27 | Chimeric 22C3 Fab: Rat Fc heavy chain |
| 28 | Chimeric 22C3 Fab: Rat Fc light chain |
| 29 | Antibody 20C3 heavy chain variable region |
| 30 | Antibody 20C3 light chain variable region |

REFERENCES

1. Sharpe, A. H, et al., *Nature Immunology* 8:239-245 (2007).
2. Dong H et al. *Nat Med.* 8(8):793-800 (2002).
3. Yang et al., *Invest Ophthalmol Vis Sci.* 49:2518-2525 (2008).
4. Ghebeh et al. *Neoplasia* 8: 190-198 (2006).
5. Hamanishi J et al., *Proceeding of the National Academy of Sciences* 104: 3360-3365 (2007).
6. Nomi, T. Et al., *Clinical Cancer Research* 13:2151-2157 (2007).
8. Ohigashi Y et al., *Clin. Cancer Research* 11: 2947-2953 (2005).
9. Inman et al., *Cancer* 109: 1499-1505 (2007).
10. Shimauchi T et al., *Int. J. Cancer* 121:2585-2590 (2007).
11. Gao et al., *Clinical Cancer Research* 15: 971-979 (2009).
12. Nakanishi *J., Cancer Immunol Immunother.* 56:1173-1182 (2007).

13. Hino et al., *Cancer* 116 (7):1757-1766 (2010).
14. Ghebeh H., *BMC Cancer.* 8:57 (2008).
15. Ahmadzadeh M et al., *Blood* 114: 1537-1544 (2009).
16. Thompson R. H. et al., *Clinical Cancer Research* 15: 1757-1761 (2007).
17. Toplian, S. L. et al., *New Eng. J Med.* 366 (26): 2443-2454 (2012).
18. Hamid, O. et al., *New Eng. J Med.* 369: 134-144 (2013).
19. Spigel, D. R. et al., *J. Clin. Oncol.* 31: Suppl, abstr 8008 (2013)
20. Thompson, R. H., et al., *PNAS* 101 (49): 17174-17179 (2004).
21. Thompson, R. H. et al., *Cancer Res.* 66: 3381-3385 (2006).
22. Gadiot, J., et al., *Cancer* 117:2192-2201 (2011).
23. Taube, J. M. et al., *Sci Transl Med* 4 (127): 127ra37 (2012).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating a human patient having a tumor, which comprises:
   (1) obtaining a PD-1:PD-Ligand proximity score for a tumor sample from the patient;
   wherein the PD-1:PD-Ligand proximity score has been assigned to the tumor sample by a process which comprises:
      (a) obtaining an image of tissue that has been removed from the tumor sample and immunohistochemically stained for PD-1 and PD-Ligand expression in a manner that allows stained PD-1 cells to be distinguished from stained PD-Ligand cells;
      (b) defining in the image one or more regions of interest (ROIs) that comprises neoplastic cells and associated stroma, wherein substantially all of the neoplastic cells and associated stroma in the image are contained in the defined ROIs;
      (c) randomly creating across each defined ROI a plurality of subregions of substantially the same shape and size, wherein each of the subregions defines an area that is large enough to include a spatially proximal pair of a stained PD-1 cell and a stained PD-Ligand cell and small enough to exclude pairs of stained PD-1 and PD-Ligand cells that are not spatially proximal; and
      (d) calculating the percent of all of the subregions that are positive for both stained PD-1 cells and stained PD-Ligand cells to generate the PD-1:PD-ligand proximity score for the tumor sample,
   (2) comparing the PD-1:PD-Ligand proximity score for the tumor sample with a threshold PD-1:PD-Ligand proximity score,
   (3) classifying the tumor as biomarker positive or biomarker negative,
   wherein if the proximity score for the tumor sample is equal to or greater than the threshold proximity score, then the tumor is classified as positive for the PD-1:PD-Ligand proximity biomarker, and if the obtained score is less than the threshold score, then the tumor is classified as negative for the PD-1:PD-Ligand proximity biomarker, and
   (4) administering to the patient a PD-1 antagonist if the tumor is positive for the PD-1:PD-Ligand proximity biomarker and administering to the subject a cancer treatment that does not include a PD-1 antagonist if the tumor is negative for the PD-1:PD-Ligand proximity biomarker.

2. The method of claim 1, wherein the steps (1)-(3) further comprise obtaining a tumor sample from the patient, sending the tumor sample to a diagnostic laboratory, and receiving from the diagnostic laboratory a report that states whether the tumor sample is positive or negative for the PD-1:PD-Ligand proximity biomarker.

3. The method of claim 1, wherein the tumor sample is from a human diagnosed with bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC) or triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

4. The method of claim 1 wherein the tumor sample is from a human diagnosed with melanoma or non small cell lung cancer (NSCLC), the PD-Ligand is PD-L1, and the PD-1 antagonist is nivolumab or an antibody comprising a heavy chain comprising a sequence of amino acids as set forth in SEQ JD NO:21 and alight chain comprising a sequence of amino acids as set forth in SEQ ID NO:22.

5. The method of claim 1, wherein the tumor sample is from a human diagnosed with metastatic melanoma, the PD-1 antagonist is an antibody comprising a heavy chain comprising a sequence of amino acids as set forth in SEQ ID NO:21 and a light chain comprising a sequence of amino acids as set forth in SEQ ID NO:22, the PD-Ligand is PD-L1 and the threshold PD-1:PD-Ligand proximity score is about 0.2%.

6. The method of claim 1, wherein the image represents the entirety of the stained tissue and only one ROI is defined for the image or wherein the image represents the entirety of the stained tissue and two or more ROIs are defined for the image.

7. The method of claim 1, wherein the tumor sample has also been immunohistochemically stained for expression of a worker protein specific for the type of tumor comprising the tumor sample.

8. The method of claim 7, wherein the tissue has been immunohistochemically stained for the expression of PD-L1, PD-L2 or both PD-L1 and PD-L2.

9. The method of claim 8, wherein the tissue has been counterstained with a nuclear stain.

10. The method of claim 8, wherein the image is obtained by a method comprising:
   obtaining a tissue section from the tumor sample,
   contacting the tissue section with an antibody specific for PD-1 (anti-PD-1 Ab) under conditions suitable for forming antibody-antigen complexes, and
   washing the tissue section to remove unbound antibody and detecting antibody-antigen complexes comprising the PD-1 antibody,
   contacting the tissue section with an antibody specific for PD-Ligand (anti-PD-Ligand Ab) under conditions suitable for forming antibody-antigen complexes, and
   washing the tissue section to remove unbound antibody and detecting antibody-antigen complexes comprising the PD-Ligand antibody,
   wherein steps (b) and (c) are performed before or after steps (d) and (e), or
   wherein steps (b) and (d) are performed simultaneously and steps (c) and (e) are performed simultaneously.

11. The method of claim 8, wherein the image is obtained by a method comprising:
   obtaining at least two adjacent tissue sections that have been stained in separate monoplex immunohistochemistry (IHC) assays, wherein one of the tissue sections has been stained for PD-1 using the anti-PD-1 Ab and the other tissue section has been stained for the PD-Ligand using the anti-PD-Ligand Ab,
   creating a registered digital image of each of the stained tissue sections, and
   superimposing the registered digital images to generate a composite image.

12. The method of claim 11, wherein the anti-PD-Ligand Ab is specific for PD-L1 or is a bispecific antibody that binds both PD-L1 and PD-L2.

13. The method of claim 12, wherein the immunohistochemically stained tissue is obtained using a direct immunohistochemistry (IHC) assay or an indirect INC assay.

14. The method of claim 1, wherein the PD-1 cells are stained with a first detectable label and the PD-Ligand cells are stained with a second detectable label that is distinguishable from the first label, wherein the first and second detectable labels are first and second colors produced by fluorophores or chromogens.

15. The method of claim 14, wherein the image is a digital image and the process further comprises:
   segmenting the ROI to extract a first set of pixels for the first color and a second set of pixels for the second color,
   assigning a positive value to each of the ROI subregions that has a pixel from each of the first and second extracted pixel sets, and
   assigning a negative value to each of the ROI subregions that lacks a pixel from either of the first and second extracted pixel sets,
   wherein the segmenting step occurs prior to creating the subregions in the one or more ROIs.

16. The method of claim 15, which further comprises examining the image for fluorescing artifacts and removing any detected artifacts from the image, wherein the examining is performed prior to the segmenting step.

17. The method of claim 1, wherein the area covered by each of the subregions is selected such that it captures physiologic interactions between a single PD-Ligand positive cell and a single PD-1 positive cell.

18. The method of claim 15, wherein the image is magnified 200 times and the subregions are discs with radii in the range of 2-10 pixels.

* * * * *

SEQUENCE LISTING

```
<160> NUMBER OF SEQ ID NOS: 30

<210> SEQ ID NO 1
<211> LENGTH: 15
<212> TYPE: PRT
<213> ORGANISM: Artificial
<220> FEATURE:
<223> OTHER INFORMATION: Antibody Light Chain CDR

<400> SEQUENCE: 1

Arg Ala Ser Lys Ser Val Ser Thr Ser Gly Phe Ser Tyr Leu His
1               5                   10                  15

<210> SEQ ID NO 2
<211> LENGTH: 7
<212> TYPE: PRT
<213> ORGANISM: Artificial
<220> FEATURE:
<223> OTHER INFORMATION: Antibody Light Chain CDR

<400> SEQUENCE: 2

Leu Ala Ser Asn Leu Glu Ser
1               5

<210> SEQ ID NO 3
<211> LENGTH: 9
<212> TYPE: PRT
<213> ORGANISM: Artificial
<220> FEATURE:
<223> OTHER INFORMATION: Antibody Light Chain CDR

<400> SEQUENCE: 3

Gln His Ser Trp Glu Leu Pro Leu Thr
1               5

<210> SEQ ID NO 4
<211> LENGTH: 5
<212> TYPE: PRT
<213> ORGANISM: Artificial
<220> FEATURE:
```

```
<223> OTHER INFORMATION: Antibody Heavy Chain CDR

<400> SEQUENCE: 4

Ser Tyr Tyr Leu Tyr
1               5

<210> SEQ ID NO 5
<211> LENGTH: 17
<212> TYPE: PRT
<213> ORGANISM: Artificial
<220> FEATURE:
<223> OTHER INFORMATION: Antibody Heavy Chain CDR

<400> SEQUENCE: 5

Gly Val Asn Pro Ser Asn Gly Gly Thr Asn Phe Ser Glu Lys Phe Lys
1               5                   10                  15

Ser

<210> SEQ ID NO 6
<211> LENGTH: 11
<212> TYPE: PRT
<213> ORGANISM: Artificial
<220> FEATURE:
<223> OTHER INFORMATION: Antibody Heavy Chain CDR

<400> SEQUENCE: 6

Arg Asp Ser Asn Tyr Asp Gly Gly Phe Asp Tyr
1               5                   10

<210> SEQ ID NO 7
<211> LENGTH: 15
<212> TYPE: PRT
<213> ORGANISM: Artificial
<220> FEATURE:
<223> OTHER INFORMATION: Antibody Light Chain CDR

<400> SEQUENCE: 7

Arg Ala Ser Lys Gly Val Ser Thr Ser Gly Tyr Ser Tyr Leu His
1               5                   10                  15

<210> SEQ ID NO 8
<211> LENGTH: 7
<212> TYPE: PRT
<213> ORGANISM: Artificial
<220> FEATURE:
<223> OTHER INFORMATION: Antibody Light Chain CDR

<400> SEQUENCE: 8

Leu Ala Ser Tyr Leu Glu Ser
1               5

<210> SEQ ID NO 9
<211> LENGTH: 9
<212> TYPE: PRT
<213> ORGANISM: Artificial
<220> FEATURE:
<223> OTHER INFORMATION: Antibody Light Chain CDR

<400> SEQUENCE: 9

Gln His Ser Arg Asp Leu Pro Leu Thr
1               5

<210> SEQ ID NO 10
<211> LENGTH: 5
<212> TYPE: PRT
<213> ORGANISM: Artificial
```

<220> FEATURE:
<223> OTHER INFORMATION: Antibody Heavy Chain CDR

<400> SEQUENCE: 10

Asn Tyr Tyr Met Tyr
1               5

<210> SEQ ID NO 11
<211> LENGTH: 17
<212> TYPE: PRT
<213> ORGANISM: Artificial
<220> FEATURE:
<223> OTHER INFORMATION: Antibody Heavy Chain CDR

<400> SEQUENCE: 11

Gly Ile Asn Pro Ser Asn Gly Gly Thr Asn Phe Asn Glu Lys Phe Lys
1               5                   10                  15

Asn

<210> SEQ ID NO 12
<211> LENGTH: 11
<212> TYPE: PRT
<213> ORGANISM: Artificial
<220> FEATURE:
<223> OTHER INFORMATION: Antibody Heavy Chain CDR

<400> SEQUENCE: 12

Arg Asp Tyr Arg Phe Asp Met Gly Phe Asp Tyr
1               5                   10

<210> SEQ ID NO 13
<211> LENGTH: 120
<212> TYPE: PRT
<213> ORGANISM: Artificial
<220> FEATURE:
<223> OTHER INFORMATION: Humanized Antibody Heavy Chain Variable Region

<400> SEQUENCE: 13

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 14
<211> LENGTH: 447
<212> TYPE: PRT
<213> ORGANISM: Artificial
<220> FEATURE:
<223> OTHER INFORMATION: Humanized Antibody Heavy Chain

<400> SEQUENCE: 14

-continued

```
Gln Val Gln Leu Val Gln Ser Gly Val Glu Val Lys Pro Gly Ala
 1               5                  10                 15

Ser Val Lys Val Ser Cys Lys Ala Ser Gly Tyr Thr Phe Thr Asn Tyr
             20                  25                  30

Tyr Met Tyr Trp Val Arg Gln Ala Pro Gly Gln Gly Leu Glu Trp Met
         35                  40                  45

Gly Gly Ile Asn Pro Ser Asn Gly Gly Thr Asn Phe Asn Glu Lys Phe
     50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
                210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415
```

```
Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 15
<211> LENGTH: 111
<212> TYPE: PRT
<213> ORGANISM: Artificial
<220> FEATURE:
<223> OTHER INFORMATION: Humanized Antibody Light Chain Variable Region

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 16
<211> LENGTH: 111
<212> TYPE: PRT
<213> ORGANISM: Artificial
<220> FEATURE:
<223> OTHER INFORMATION: Humanized Antibody Light Chain Variable Region

<400> SEQUENCE: 16

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys
            100                 105                 110

<210> SEQ ID NO 17
<211> LENGTH: 111
<212> TYPE: PRT
<213> ORGANISM: Artificial
<220> FEATURE:
<223> OTHER INFORMATION: Humanized Antibody Light Chain Variable Region

<400> SEQUENCE: 17

Asp Ile Val Met Thr Gln Thr Pro Leu Ser Leu Pro Val Thr Pro Gly
```

```
1               5                   10                  15
Glu Pro Ala Ser Ile Ser Cys Arg Ala Ser Lys Gly Val Ser Thr Ser
            20                  25                  30
Gly Tyr Ser Tyr Leu His Trp Tyr Leu Gln Lys Pro Gly Gln Ser Pro
            35                  40                  45
Gln Leu Leu Ile Tyr Leu Ala Ser Tyr Leu Glu Ser Gly Val Pro Asp
50                      55                  60
Arg Phe Ser Gly Ser Gly Ser Gly Thr Ala Phe Thr Leu Lys Ile Ser
65                      70                  75                  80
Arg Val Glu Ala Glu Asp Val Gly Leu Tyr Tyr Cys Gln His Ser Arg
                85                  90                  95
Asp Leu Pro Leu Thr Phe Gly Gln Gly Thr Lys Leu Glu Ile Lys
            100                 105                 110
```

<210> SEQ ID NO 18
<211> LENGTH: 218
<212> TYPE: PRT
<213> ORGANISM: Artificial
<220> FEATURE:
<223> OTHER INFORMATION: Humanized Antibody Light Chain

<400> SEQUENCE: 18

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
            20                  25                  30
Gly Tyr Ser Tyr Leu His Trp Tyr Gln Gln Lys Pro Gly Gln Ala Pro
            35                  40                  45
Arg Leu Leu Ile Tyr Leu Ala Ser Tyr Leu Glu Ser Gly Val Pro Ala
        50                  55                  60
Arg Phe Ser Gly Ser Gly Ser Gly Thr Asp Phe Thr Leu Thr Ile Ser
65                      70                  75                  80
Ser Leu Glu Pro Glu Asp Phe Ala Val Tyr Tyr Cys Gln His Ser Arg
                85                  90                  95
Asp Leu Pro Leu Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
            115                 120                 125
Leu Lys Ser Gly Thr Ala Ser Val Val Cys Leu Leu Asn Asn Phe Tyr
        130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 19
<211> LENGTH: 218
<212> TYPE: PRT
<213> ORGANISM: Artificial
<220> FEATURE:
<223> OTHER INFORMATION: Humanized Antibody Light Chain

<400> SEQUENCE: 19

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 20
<211> LENGTH: 218
<212> TYPE: PRT
<213> ORGANISM: Artificial
<220> FEATURE:
<223> OTHER INFORMATION: Humanized Antibody Light Chain

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
    210                 215

<210> SEQ ID NO 21
<211> LENGTH: 447
<212> TYPE: PRT
<213> ORGANISM: Artificial
<220> FEATURE:
<223> OTHER INFORMATION: Humanized Antibody Heavy Chain

<400> SEQUENCE: 21

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270
```

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 22
<211> LENGTH: 218
<212> TYPE: PRT
<213> ORGANISM: Artificial
<220> FEATURE:
<223> OTHER INFORMATION: Humanized Antibody Light Chain

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 23
<211> LENGTH: 440
<212> TYPE: PRT
<213> ORGANISM: Homo sapiens

<400> SEQUENCE: 23

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

```
Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 24
<211> LENGTH: 214
<212> TYPE: PRT
<213> ORGANISM: Homo sapiens

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 446
<212> TYPE: PRT
<213> ORGANISM: Mus musculus

<400> SEQUENCE: 25

Gln Val His Leu Gln Gln Ser Gly Ala Glu Leu Ala Lys Pro Gly Ala
1               5                   10                  15
```

```
Ser Val Lys Met Ser Cys Lys Ala Ser Gly Tyr Thr Phe Thr Ser Tyr
         20                  25                  30

Trp Ile His Trp Ile Lys Gln Arg Pro Gly Gln Gly Leu Glu Trp Ile
         35                  40                  45

Gly Tyr Ile Asn Pro Ser Ser Gly Tyr His Glu Tyr Asn Gln Lys Phe
 50                  55                  60

Ile Asp Lys Ala Thr Leu Thr Ala Asp Arg Ser Ser Ser Thr Ala Tyr
 65                  70                  75                  80

Met His Leu Thr Ser Leu Thr Ser Glu Asp Ser Ala Val Tyr Tyr Cys
                 85                  90                  95

Ala Arg Ser Gly Trp Leu Ile His Gly Asp Tyr Phe Asp Phe Trp
                100                 105                 110

Gly Gln Gly Thr Thr Leu Thr Val Ser Ser Ala Lys Thr Thr Pro Pro
        115                 120                 125

Ser Val Tyr Pro Leu Ala Pro Gly Ser Ala Ala Gln Thr Asn Ser Met
130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
                180                 185                 190

Pro Ser Ser Thr Trp Pro Ser Glu Thr Val Thr Cys Asn Val Ala His
            195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
                260                 265                 270

Gln Phe Ser Trp Phe Val Asp Asp Val Glu Val His Thr Ala Gln Thr
            275                 280                 285

Gln Pro Arg Glu Glu Gln Phe Asn Ser Thr Phe Arg Ser Val Ser Glu
290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
                340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
                420                 425                 430
```

Asn His His Thr Glu Lys Ser Leu Ser His Ser Pro Gly Lys
             435                 440                 445

<210> SEQ ID NO 26
<211> LENGTH: 219
<212> TYPE: PRT
<213> ORGANISM: Mus musculus

<400> SEQUENCE: 26

Asp Ile Val Met Ser Gln Ser Pro Ser Ser Leu Ala Val Ser Ala Gly
1               5                   10                  15

Glu Lys Val Thr Met Thr Cys Lys Ser Gln Ser Leu Leu His Thr
            20                  25                  30

Ser Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asp Val Val Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 27
<211> LENGTH: 448
<212> TYPE: PRT
<213> ORGANISM: Artificial
<220> FEATURE:
<223> OTHER INFORMATION: Chimeric antibody heavy chain

<400> SEQUENCE: 27

Gln Val His Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Ile His Trp Ile Lys Gln Arg Pro Gly Gln Gly Leu Glu Trp Ile
        35                  40                  45

Gly Tyr Ile Asn Pro Ser Ser Gly Tyr His Glu Tyr Asn Gln Lys Phe
    50                  55                  60

Ile Asp Lys Ala Thr Leu Thr Ala Asp Arg Ser Ser Ser Thr Ala Tyr
65                  70                  75                  80

Met His Leu Thr Ser Leu Thr Ser Glu Asp Ser Ala Val Tyr Tyr Cys

```
                    85                  90                  95
Ala Arg Ser Gly Trp Leu Ile His Gly Asp Tyr Tyr Phe Asp Phe Trp
                100                 105                 110

Gly Gln Gly Thr Thr Leu Thr Val Ser Ser Ala Glu Thr Thr Ala Pro
            115                 120                 125

Ser Val Tyr Pro Leu Ala Pro Gly Thr Ala Leu Lys Ser Asn Ser Met
        130                 135                 140

Val Thr Leu Gly Cys Leu Val Lys Gly Tyr Phe Pro Glu Pro Val Thr
145                 150                 155                 160

Val Thr Trp Asn Ser Gly Ala Leu Ser Ser Gly Val His Thr Phe Pro
                165                 170                 175

Ala Val Leu Gln Ser Gly Leu Tyr Thr Leu Thr Ser Ser Val Thr Val
            180                 185                 190

Pro Ser Ser Thr Trp Pro Ser Gln Thr Val Thr Cys Asn Val Ala His
        195                 200                 205

Pro Ala Ser Ser Thr Lys Val Asp Lys Lys Ile Val Pro Arg Asn Cys
    210                 215                 220

Gly Gly Asp Cys Lys Pro Cys Ile Cys Thr Gly Ser Glu Val Ser Ser
225                 230                 235                 240

Val Phe Ile Phe Pro Pro Lys Pro Lys Asp Val Leu Thr Ile Thr Leu
                245                 250                 255

Thr Pro Lys Val Thr Cys Val Val Val Asp Ile Ser Gln Asp Asp Pro
            260                 265                 270

Glu Val His Phe Ser Trp Phe Val Asp Asp Val Glu Val His Thr Ala
        275                 280                 285

Gln Thr Arg Pro Pro Glu Glu Gln Phe Asn Ser Thr Phe Arg Ser Val
    290                 295                 300

Ser Glu Leu Pro Ile Leu His Gln Asp Trp Leu Asn Gly Arg Thr Phe
305                 310                 315                 320

Arg Cys Lys Val Thr Ser Ala Ala Phe Pro Ser Pro Ile Glu Lys Thr
                325                 330                 335

Ile Ser Lys Pro Glu Gly Arg Thr Gln Val Pro His Val Tyr Thr Met
            340                 345                 350

Ser Pro Thr Lys Glu Glu Met Thr Gln Asn Glu Val Ser Ile Thr Cys
        355                 360                 365

Met Val Lys Gly Phe Tyr Pro Pro Asp Ile Tyr Val Glu Trp Gln Met
    370                 375                 380

Asn Gly Gln Pro Gln Glu Asn Tyr Lys Asn Thr Pro Pro Thr Met Asp
385                 390                 395                 400

Thr Asp Gly Ser Tyr Phe Leu Tyr Ser Lys Leu Asn Val Lys Lys Glu
                405                 410                 415

Lys Trp Gln Gln Gly Asn Thr Phe Thr Cys Ser Val Leu His Glu Gly
            420                 425                 430

Leu His Asn His His Thr Glu Lys Ser Leu Ser His Ser Pro Gly Lys
        435                 440                 445

<210> SEQ ID NO 28
<211> LENGTH: 216
<212> TYPE: PRT
<213> ORGANISM: Artificial
<220> FEATURE:
<223> OTHER INFORMATION: Chimeric Antibody Light Chain

<400> SEQUENCE: 28

Met Ser Gln Ser Pro Ser Ser Leu Ala Val Ser Ala Gly Glu Lys Val
```

-continued

```
1               5                   10                  15
Thr Met Thr Cys Lys Ser Ser Gln Ser Leu Leu His Thr Ser Thr Arg
            20                  25                  30
Lys Asn Tyr Leu Ala Trp Tyr Gln Gln Lys Pro Gly Gln Ser Pro Lys
            35                  40                  45
Leu Leu Ile Tyr Trp Ala Ser Thr Arg Glu Ser Gly Val Pro Asp Arg
50                  55                  60
Phe Thr Gly Ser Gly Ser Gly Thr Asp Phe Thr Leu Thr Ile Ser Ser
65                  70                  75                  80
Val Gln Ala Glu Asp Leu Ala Val Tyr Tyr Cys Lys Gln Ser Tyr Asp
            85                  90                  95
Val Val Thr Phe Gly Ala Gly Thr Lys Leu Glu Leu Lys Arg Ala Asp
            100                 105                 110
Ala Ala Pro Thr Val Ser Ile Phe Pro Pro Ser Thr Glu Gln Leu Ala
            115                 120                 125
Thr Gly Gly Ala Ser Val Val Cys Leu Met Asn Asn Phe Tyr Pro Arg
            130                 135                 140
Asp Ile Ser Val Lys Trp Lys Ile Asp Gly Thr Glu Arg Arg Asp Gly
145                 150                 155                 160
Val Leu Asp Ser Val Thr Asp Gln Asp Ser Lys Asp Ser Thr Tyr Ser
            165                 170                 175
Met Ser Ser Thr Leu Ser Leu Thr Lys Ala Asp Tyr Glu Ser His Asn
            180                 185                 190
Leu Tyr Thr Cys Glu Val Val His Lys Thr Ser Ser Ser Pro Val Val
            195                 200                 205
Lys Ser Phe Asn Arg Asn Glu Cys
            210                 215
```

<210> SEQ ID NO 29
<211> LENGTH: 122
<212> TYPE: PRT
<213> ORGANISM: Mus musculus

<400> SEQUENCE: 29

```
Gln Val Gln Val Gln Gln Ser Gly Ala Glu Leu Ala Glu Pro Gly Ala
1               5                   10                  15
Ser Val Lys Met Ser Cys Lys Ala Ser Gly Tyr Ile Phe Thr Ser Tyr
            20                  25                  30
Trp Met His Trp Leu Lys Gln Arg Pro Gly Gln Gly Leu Glu Trp Ile
            35                  40                  45
Gly Tyr Ile Asn Pro Ser Ser Asp Tyr Asn Glu Tyr Ser Glu Lys Phe
50                  55                  60
Met Asp Lys Ala Thr Leu Thr Ala Asp Lys Ala Ser Thr Thr Ala Tyr
65                  70                  75                  80
Met Gln Leu Ile Ser Leu Thr Ser Glu Asp Ser Ala Val Tyr Tyr Cys
            85                  90                  95
Ala Arg Ser Gly Trp Leu Val His Gly Asp Tyr Tyr Phe Asp Tyr Trp
            100                 105                 110
Gly Gln Gly Thr Thr Leu Thr Val Ser Ser
            115                 120
```

<210> SEQ ID NO 30
<211> LENGTH: 112
<212> TYPE: PRT
<213> ORGANISM: Mus musculus

```
<400> SEQUENCE: 30

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asp Val Val Thr Phe Gly Ala Gly Thr Lys Leu Glu Leu Lys
                100                 105                 110
```